United States Patent
Wang et al.

(10) Patent No.: US 11,702,628 B2
(45) Date of Patent: Jul. 18, 2023

(54) PERFUSION MEDIUM FOR CULTURING MAMMALIAN CELLS AND REDUCING CELL BLEED IN A PERFUSION CELL CULTURE

(71) Applicant: Boehringer Ingelheim International GmbH, Ingelheim am Rhein (DE)

(72) Inventors: Samantha Wang, San Francisco, CA (US); Henry Lin, Westfield, NJ (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 863 days.

(21) Appl. No.: 16/496,527

(22) PCT Filed: Mar. 27, 2018

(86) PCT No.: PCT/EP2018/057757
§ 371 (c)(1),
(2) Date: Sep. 23, 2019

(87) PCT Pub. No.: WO2018/178069
PCT Pub. Date: Oct. 4, 2018

(65) Prior Publication Data
US 2020/0377849 A1 Dec. 3, 2020

Related U.S. Application Data

(60) Provisional application No. 62/479,422, filed on Mar. 31, 2017.

(51) Int. Cl.
*C12N 5/00* (2006.01)
*C12P 21/02* (2006.01)

(52) U.S. Cl.
CPC .......... *C12N 5/0037* (2013.01); *C12P 21/02* (2013.01); *C12N 2500/12* (2013.01)

(58) Field of Classification Search
CPC .... C12N 5/0037; C12N 2500/12; C12P 21/02
See application file for complete search history.

(56) References Cited

U.S. PATENT DOCUMENTS

2013/0122543 A1* 5/2013 Leist ................. C12N 5/005
435/69.1

FOREIGN PATENT DOCUMENTS

| JP | H01247097 A | 10/1989 |
|---|---|---|
| WO | 199748808 A1 | 12/1997 |
| WO | 2008033517 A2 | 3/2008 |
| WO | 2011134920 A1 | 11/2011 |
| WO | 2013006479 A2 | 1/2013 |

OTHER PUBLICATIONS

International Search Report for PCT/EP2018/057757 dated Jul. 6, 2018.

Yoon, Sung Kwan et al. "Adaptation of Chinese Hamster Ovary Cells to High Potassium Ion-Containing Medium for Enhancement of Follicle-Stimulating Hormone Production" (2007) Biotechnology and Bioprocess Engineering, 12, 399-403.
Wang, Samantha B. et al. "Manipulation of the sodium-potassium ratio as a lever for controlling cell growth and improving cell specific productivity in perfusion CHO cell cultures" (2018) Biotechnology and Bioengineering, 115, 921-931.
Fong, Wangfun et al. "Optimization of monoclonal antibody production: combined effects of potassium acetate and perfusion in a stirred tank bioreactor" (1997) Cytotechnology, 24, 47-54.
Kompala, Dhinakar S. et al. "Optimization of High Cell Denisty Perfusion Bioreactors" (2006) Cell Culture Technology for Pharmaceutical and Cell Based Therapies, 387-416.
Orr, C.W. et al. "Potassium: Effect on DNA Synthesis and Multiplication of Baby-Hamster Kidney Cells" (1972) Proc. Nat. Acad. Sci., vol. 69, No. 1, 243-247.
Pau, M.G. et al. "The human cell line PER C6 provides a new manufacturing system for the production of influenza vaccines" (2001) Vaccine, 19, 2716-2721.
Pitot, H.C. et al. "Hepatomas in Tissue Culture Compared with Adapting Liver In Vivo" (1964) National Cancer Institute Monographs, vol. 13, 229-245.
Reuber, Melvin D. et al. "A Transplantable Bile-Secreting Hepatocellular Carcinoma in the Rat" (1961) Journal Natl Cancer Inst. vol. 26, 891-899.
Sato, S. et al. "Stimulation of monoclonal antibody production by human-human hybridoma cells with an elevated concentration of potassium or sodium phosphate in serum-free medium" (1989) Cytotechnology, 2, 63-67.
Suzuki, E. et al. "Enhanced Antibody Production at Slowed Growth Rates: Experimental Demonstration an a Simple Structured Model" (1990) Biotechnol. Prog., vol. 6, 231-236.
Takagi, M et al. "Effects of Osmotic Pressure on Metabolism of CHO Cells Producing Tissue Plasminogen Activator in Adhesion Culture Compared with that in Suspension Culture" (1998), JAACT and ESACT Meeting, 2 pgs (English Translation).
Takagi, Mutsumi et al. "The effect of osmolarity on metabolism and morphology in adhesion and suspension Chinese hamster ovary cells producing tissue plasminogen activator" (2000) Cytotechnology, 32, 171-179.
Urlaub, Gail et al. "Deletion of the Diploid Dihydrofolate Reductase Locus from Cultured Mammalian Cells" (1983) Cell, vol. 33, 405-412.

(Continued)

*Primary Examiner* — Robert S Landsman
(74) *Attorney, Agent, or Firm* — Mary Breen Smith

(57) ABSTRACT

The invention relates to a method of culturing mammalian cells expressing a heterologous protein in a perfusion cell culture comprising increasing the potassium concentration and decreasing the molar ratio of sodium to potassium to reduce wasteful cell bleed and to increase protein production. The invention further relates to a serum-free perfusion medium comprising a high potassium ion concentration and a low molar ratio of sodium to potassium and to the use of this medium for use in culturing cells in a perfusion culture during production phase or for reducing the cell bleed volume during production phase.

11 Claims, 7 Drawing Sheets

(56) References Cited

OTHER PUBLICATIONS

Woelfel, Jens et al. "CAP-T cell expression system: a novel rapid and versatile human cell expression system for fast and high yield transient protein expression" (2011) BMC Proceedings, 5 (Supp 8) P133, 2 pgs.

* cited by examiner (C)

(D)

(A)

(B)

(C)

(D)

PERFUSION MEDIUM FOR CULTURING MAMMALIAN CELLS AND REDUCING CELL BLEED IN A PERFUSION CELL CULTURE

TECHNICAL FIELD

The invention relates to a method of culturing mammalian cells expressing a heterologous protein in a perfusion cell culture comprising increasing the potassium concentration and decreasing the molar ratio of sodium to potassium to reduce wasteful cell bleed and to increase protein production. The invention further relates to a serum-free perfusion medium comprising a high potassium ion concentration and a low molar ratio of sodium to potassium and to the use of this medium for use in culturing cells in a perfusion culture during production phase or for reducing the cell bleed volume during production phase.

BACKGROUND

Three methods are typically used in commercial processes for the production of recombinant proteins by mammalian cell culture: batch culture, fed-batch culture, and perfusion culture.

Perfusion based methods offer potential improvement over the batch and fed-batch methods by adding fresh media and simultaneously removing spent media. Large scale commercial cell culture strategies may reach high cell densities of 60-90×$10^6$ cells/mL, at which point about a third to over half of the reactor volume may be biomass. With perfusion based culture, extreme cell densities of >1×$10^8$ cells/mL have been achieved. Typical perfusion cultures begin with a batch culture start-up lasting for a day or more to enable rapid initial cell growth and biomass accumulation, followed by continuous, step-wise and/or intermittent addition of fresh perfusion media to the culture and simultaneous removal of spent media with retention of cells throughout the growth and production phases of the culture. Various methods, such as sedimentation, centrifugation, or filtration, can be used to remove spent media, while maintaining the cells. Perfusion flow rates of a fraction of a working volume per day up to many multiple working volumes per day have been utilized.

Continuous processing for biologics manufacturing has numerous advantages over traditional fed batch, but many challenges still remain. Improvements in media have achieved higher viable cell densities (VCD) and, in turn, higher titers in perfusion processes. However, these elevated cell densities can become unsustainable resulting in viability loss and shortening of the perfusion run. Increased media preparation, use, storage and disposal are necessary to support a long term perfusion culture, particularly those with high cell densities, which also need even more nutrients, and all of this drives the production costs even higher, compared to batch and fed batch methods.

Potassium and sodium ion concentration are important environmental factors for cells in culture. Internal ion concentrations are kept remarkably constant by cells and potassium and sodium are mainly responsible for the membrane potential across the cell membrane. Typically in vivo intracellular sodium and potassium ion concentrations are around 12 mM and 139 mM, respectively and typical in vivo sodium and potassium ion concentrations outside the cell are around 145 mM and 4 mM, respectively. First observations that a higher potassium concentration may have an inhibitory effect on cell proliferation were made in the early 1970s, however, so far this was not successfully used to improve perfusion cell culture.

Orr et al. (Proc. Nat. Acad. Sci. USA (1972) 69(1): 243-247), discloses that potassium concentrations of 114 mM ($Na^+/K^+$=0.53) inhibit cell proliferation in monolayer BHK cells using Ham's F12 medium containing 12% calf serum or an equivalent medium wherein sodium has been replaced by potassium. Potassium concentrations of 36 to 72 mM actually increased cell density. In cultures with potassium concentrations higher than 128 mM cells soon rounded up, detached from the plate and died. Morphological changes were also reported for cells treated with 114 mM. This document lacks any indication that increased potassium concentrations would be beneficial in perfusion cell culture to control cell bleeding or improving productivity.

JP H01247097A discloses that treatment of hybridoma cell perfusion cultures with 30 mM potassium chloride in serum-free medium increased antibody production (titer and cell specific productivity) and simultaneously reduced cell proliferation rate and cell viability. Thus, increasing the potassium chloride concentration seems to reduce viability. Also the increased protein production seems to be linked to the reduced viability.

WO 2011/134920 discloses a chemically defined cell culture medium for CHO cells comprising a molar ratio of sodium to potassium between 10:1 and 1:1 and a potassium concentration of about 8 to about 12 mM for fed batch culture.

Sato et al. (Cytotechnology (1989) 2: 63-67), discloses that elevated potassium and sodium phosphate concentrations in serum-free medium stimulate monoclonal antibody production in hybridoma cells. However KCl was shown to have no effect. Also, it is disclosed therein that potassium phosphate concentrations of 30 mM severely reduced viability, particularly in continuous culture. Further it teaches that increasing the sodium concentration increases productivity rather than substituting sodium with potassium.

Suzuki et al. (Biotechnol. Prog. (1990) 6(3): 231-236), discloses that treatment of hybridoma cell cultures with 10 to 100 mM potassium acetate in serum-free RPMI 1640 in batch culture resulted in growth-rate dependent antibody production. However this correlation did only apply at relatively high growth rates and viability was reduced to 58%, suggesting that sodium acetate would not be suitable for long term perfusion culture.

Fong et al. (Cytotechnology (1997) 24: 47-54), discloses that potassium acetate at a concentration about 10 mM increases antibody production in hybridoma cells while maintaining or only slightly increasing cell density in perfusion culture. However this perfusion culture was only maintained for less than 4 days in the presence of potassium acetate without disclosing viability data. Also, the observed effect could have been due to an increase in osmolarity or the acetate. The medium used was RPMI 1640 medium with 10% serum, comprising >100 mM sodium and hence the culture was not a serum-free culture and performed in a molar excess of sodium over potassium.

Yoon et al., (Biotechnology and Bioprocess Engineering (2007), 12: 399-403) discloses that high potassium ion concentrations 60 mM) increase protein production and inhibits cell growth in CHO cells in a repeated batch mode using serum-free culture medium. Potassium concentrations up to 40 mM were reported not to influence cell growth significantly and concentrations at 60 mM or higher were shown to affect cell viability. Also this document is silent on the sodium concentration.

Potassium and sodium are present in all cell culture media and altering their concentration is advantageous over having to introduce other additives, since there are no concerns regarding safety and clearance. Also when developing a culture media it is desired to keep the medium as simple as possible and limited to the essential compounds. This avoids unnecessary compounds and reduces osmolarity issues. While culture media are constantly altered and improved, there is still a need to improve perfusion culture by reducing waste and increasing productivity.

SUMMARY OF THE INVENTION

A wasteful cell bleed can be utilized to maintain a sustainable VCD and preserve viability. In continuous processes a large proportion of the culture medium and hence product is lost due to the cell "bleed" which siphons off proliferating cells and medium in order to maintain a constant, sustainable viable cell density within the bioreactor. Up to one-third of harvestable material can be lost due to cell bleed. Using a cell bleed therefore decreases the product yield per run as the product within the cell bleed is not harvested. In order to decrease the cell bleed volume and thus retain more supernatant for harvest it is therefore advantageous to inhibit cell proliferation once the desired viable cell density is reached in the production phase without affecting viability or specific protein productivity. By reducing or eliminating cell bleed, protein production is increased as compared to conventional perfusion methods. Thus, there is a need for controlling cell growth once an optimal VCD has been obtained, thus minimizing cell bleed to increase the product recovered per perfusion run, and at the same time to increase the cell specific productivity to generate a more efficient method for operating perfusion processes.

In the present invention a perfusion culture medium comprising sodium and potassium at a Na:K ratio of less than 1 and a potassium concentration of >30 mM and methods of culturing mammalian cells using said medium are provided. It is shown that the medium inhibits proliferation and increases cell specific productivity (qp) without negatively affecting viability. In particular a high potassium concentration induced cell growth arrest and a low sodium concentration increases cell specific productivity of Chinese hamster ovary (CHO) in perfusion cell culture. By controlling cell growth and thus minimizing cell bleed, the product recovered per perfusion run is greatly increased, generating a more efficient method for operating perfusion processes. This is further enhanced by the positive effect on cell specific productivity.

In one aspect a method of culturing mammalian cells expressing a heterologous protein in a perfusion cell culture is provided comprising: (a) inoculating mammalian cells expressing a heterologous protein in a serum-free culture medium; (b) culturing the mammalian cells during growth phase by perfusion with a serum-free perfusion medium; and (c) culturing the mammalian cells during production phase by perfusion with a serum-free perfusion medium comprising potassium ions at a concentration of 30 mM to 250 mM and a molar ratio of sodium to potassium ions of less than 1, wherein step (b) is optional.

In one related aspect a method of reducing cell bleeding in a perfusion cell culture expressing a heterologous protein in a perfusion cell culture is provided comprising: (a) inoculating mammalian cells expressing a heterologous protein in a serum-free culture medium; (b) culturing the mammalian cells during growth phase by perfusion with a serum-free perfusion medium; and (c) culturing the mammalian cells during production phase by perfusion with a serum-free perfusion medium comprising potassium ions at a concentration of 30 mM to 250 mM and a molar ratio of sodium to potassium ions of less than 1, wherein step (b) is optional.

In another related aspect a method of increasing protein production in a perfusion cell culture expressing a heterologous protein comprising: (a) inoculating mammalian cells expressing a heterologous protein in a serum-free culture medium; (b) culturing the mammalian cells during growth phase by perfusion with a serum-free perfusion medium; and (c) culturing the mammalian cells during production phase by perfusion with a serum-free perfusion medium comprising potassium ions at a concentration of 30 mM to 250 mM and a molar ratio of sodium to potassium ions of less than 1, wherein step (b) is optional.

Step (c) is started once the target cell density is reached. Thus, it may be started at a cell density of $10 \times 10^6$ cells/ml to about $120 \times 10^6$ cells/ml or even higher. Preferably step (c) is initiated at a cell density of at least $10 \times 10^6$ cells/ml, at least $20 \times 10^6$ cells/ml, at least $30 \times 10^6$ cells/ml, at least $40 \times 10^6$ cells/ml or at least $50 \times 10^6$ cells/ml. Most preferably step (c) is initiated at a cell density of about 30 to about $50 \times 10^6$ cells/ml.

Step (c) of the methods of the invention may further comprise maintaining a cell density by cell bleeding. Using the methods of the present invention the cell bleeding is reduced compared to a perfusion cell culture using the same serum-free perfusion medium comprising potassium ions at a concentration of less than 30 mM and a molar ratio of sodium to potassium of more than 2 and cultured under the same conditions.

In some embodiments of the methods of the invention the potassium ion concentration is about 40 mM to about 200 mM, preferably about 60 mM to about 150 mM and more preferably about 80 mM to about 100 mM. In some embodiments the molar ratio of sodium to potassium is between about 0.9 and 0.1, between about 0.8 and 0.2, between about 0.7 and 0.2, preferably between about 0.6 and 0.3 and more preferably between about 0.5 and 0.4.

According to the present invention the potassium ion is provided as one or more potassium salt. In a preferred embodiment the one or more potassium salt is selected from the group consisting of potassium bicarbonate, potassium chloride, potassium hydroxide, L-tyrosine dipotassium salt, potassium phosphate dibasic, potassium phosphate monobasic, potassium selenite, potassium pyruvic acid, potassium glutathione, potassium D-gluconate, potassium succinate and potassium ascorbate. Preferably the one or more potassium salt substitutes the corresponding sodium salt in the serum-free perfusion culture medium. More specifically the one or more potassium salt preferably substitutes the corresponding sodium salt in the serum-free perfusion medium of step b).

The osmolarity of the serum-free perfusion medium should be in the range of between 300 and 1400 mOsmol/kg, preferably between 300 and 500 mOsmol/kg, more preferably between 330 and 450 mOsmol/kg and even more preferably between 360 and 390 mOsmol/kg.

The mammalian cell may be a Chinese hamster ovary (CHO) cell, preferably a CHO-DG44 cell, a CHO-K1 cell, a CHO DXB11 cell, a CHO-S cell, a CHO GS deficient cell or a derivative of any of these cells.

The serum-free perfusion medium may be chemically defined and/or hydrolysate free. Preferably the serum-free perfusion medium is protein-free or protein-free except for recombinant insulin and/or insulin-like growth factor, more preferably the serum-free perfusion medium is chemically defined and protein-free or protein-free except for recombinant insulin and/or insulin-like growth factor.

In a further aspect a method of producing a therapeutic protein using the methods of the invention is provided optionally comprising a further step of purifying and formulating the therapeutic protein into a pharmaceutically acceptable formulation.

In another aspect a serum-free perfusion medium is provided comprising potassium ions at a concentration of 30 mM to 250 mM and a molar ratio of sodium to potassium ions of less than 1. In some embodiments the potassium ion concentration is about 40 mM to about 200 mM, preferably about 60 mM to about 150 mM and more preferably about 80 mM to about 100 mM. In some embodiments the molar ratio of sodium to potassium is between about 0.9 and 0.1, between about 0.8 and 0.2, between about 0.7 and 0.2, preferably between about 0.6 and 0.3 and more preferably between about 0.5 and 0.4.

According to the present invention the potassium ion is provided as one or more potassium salt. In a preferred embodiment the one or more potassium salt is selected from the group consisting of potassium bicarbonate, potassium chloride, potassium hydroxide, L-tyrosine dipotassium salt, potassium phosphate dibasic, potassium phosphate monobasic, potassium selenite, potassium pyruvic acid, potassium glutathione, potassium D-gluconate, potassium succinate and potassium ascorbate. Preferably the one or more potassium salt substitutes the corresponding sodium salt in the serum-free perfusion culture medium.

The osmolarity of the serum-free perfusion medium should be in the range of between 300 and 1400 mOsmol/kg, preferably between 300 and 500 mOsmol/kg, more preferably between 330 and 450 mOsmol/kg and even more preferably between 360 and 390 mOsmol/kg.

The serum-free perfusion medium may be chemically defined and/or hydrolysate free. Preferably the serum-free perfusion medium is protein-free or protein-free except for recombinant insulin and/or insulin-like growth factor, more preferably the serum-free perfusion medium is chemically defined and protein-free or protein-free except for recombinant insulin and/or insulin-like growth factor.

In yet another aspect a use of the serum-free perfusion medium of the invention for culturing mammalian cells in a perfusion culture during production phase or for reducing the total cell bleed volume in a perfusion culture is provided. Alternatively a use of the serum-free perfusion medium of the invention for increasing protein production in a perfusion cell culture is provided.

DETAILED DESCRIPTION

Figure 1:
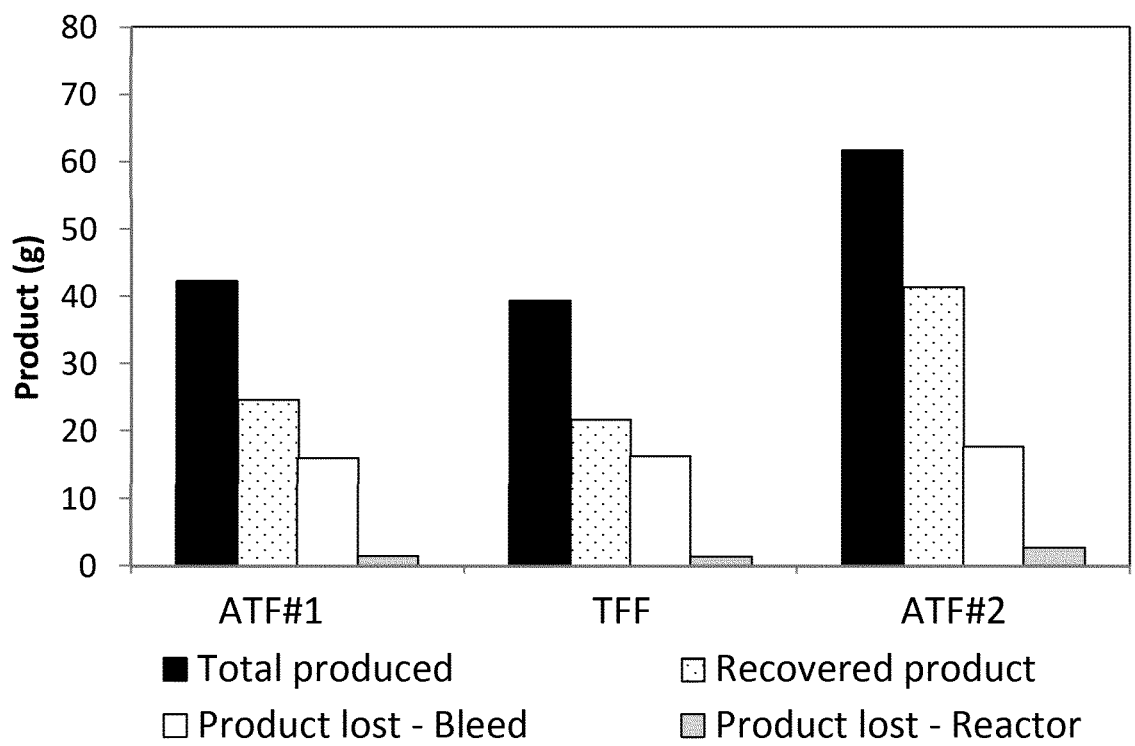
FIG. 1: Effect of cell bleed on total productivity. A CHO cell line producing monoclonal antibody mAb1 was cultured in 3 L glass perfusion bioreactors at a 2 L working volume utilizing two different recirculation devices as indicated: ATF #1 and ATF #2 were replicates using an ATF 2 device (Repligen, Waltham, Mass.) and the TFF bioreactor used a centrifugal pump (Levitronix, Zurich, Switzerland). Titer was measured for the harvest (permeate) stream (recovered product) and bioreactor contents (reactor titer) daily and the total grams produced (total produced) and product lost in the bleed and the reactor at the end of cell culture (day 29) were calculate.

The general embodiments "comprising" or "comprised" encompass the more specific embodiment "consisting of". Furthermore, singular and plural forms are not used in a limiting way. As used herein, the singular forms "a", "an"

and "the" designate both the singular and the plural, unless expressly stated to designate the singular only.

The term "perfusion" as used herein refers to maintaining a cell culture bioreactor in which equivalent volumes of media are simultaneously added and removed from the reactor while the cells are retained in the reactor. A perfusion culture may also be referred to as continuous culture. This provides a steady source of fresh nutrients and constant removal of cell waste products. Perfusion is commonly used to attain much higher cell density and thus a higher volumetric productivity than conventional bioreactor batch or fed batch conditions. Secreted protein products can be continuously harvested while retaining the cells in the reactor, e.g., by filtration, alternating tangential flow (ATF), cell sedimentation, ultrasonic separation, hydrocyclones, or any other method known to the person skilled in the art or as described Kompala and Ozturk (Cell Culture Technology for Pharmaceutical and Cell-Based Therapies, (2006), Taylor & Francis Group, LLC, pages 387-416). Mammalian cells may be grown in suspension cultures (homogeneous cultures) or attached to surfaces or entrapped in different devices (heterogeneous cultures). In order to keep the working volume in the bioreactor constant the harvest rate and cell bleed (fluid removal) should be equal to the predetermined perfusion rate. The culture is typically initiated by a batch culture and the perfusion is started on day 2-3 after inoculation when the cells are still in exponential growth phase and before nutrient limitation occurs.

Perfusion based methods offer potential improvement over the batch and fed-batch methods by adding fresh media and simultaneously removing spent media. Large scale commercial cell culture strategies may reach high cell densities of 60-90×$10^6$ cells/mL, at which point about a third to over half of the reactor volume may be biomass. With perfusion based culture, extreme cell densities of >1×$10^8$ cells/mL have been achieved. Typical perfusion cultures begin with a batch culture start-up lasting for a day or more to enable rapid initial cell growth and biomass accumulation, followed by continuous, step-wise and/or intermittent addition of fresh feed media to the culture and simultaneous removal of spent media with retention of cells throughout the growth and production phases of the culture. Various methods, such as sedimentation, centrifugation, or filtration, can be used to remove spent media, while maintaining the cells. Perfusion flow rates of a fraction of a working volume per day up to many multiple working volumes per day have been utilized.

The term "perfusion rate" as used herein is the volume added and removed and is typically measured per day. It depends on the cell density and the medium. It should be minimized to reduce the dilution of the product of interest, i.e., harvest titer, while ensuring adequate rates of nutrient addition and by-product removal. Perfusion is typically started on day 2-3 after inoculation when the cells are still in the exponential growth phase and hence perfusion rate may be increased over the culture. Increase in perfusion rate may be incremental or continuously, i.e., based on cell density or nutrient consumption. It typically starts with 0.5 or 1 vessel volume per day (VVD) and may go up to about 5 VVD. Preferably, the perfusion rate is between 0.5 to 2 VVD. The increase may be by 0.5 to 1 VVD. For continuous increase in perfusion, a biomass probe may be interfaced with the harvest pump, such that the perfusion rate is increased as a linear function of the cell density determined by the biomass probe, based on a desired cell specific perfusion rate (CSPR). The CSPR equals the perfusion rate per cell density and an ideal CSPR depend on the cell line and the cell medium. The ideal CSPR should result in optimal growth rate and productivity. A CSPR of 50 to 100 pL/cell per day may be a reasonable starting range, which can be adjusted to find the optimal rate for a specific cell line.

The term "steady state" as used herein refers to the condition where cell density and bioreactor environment remain relatively constant. This can be achieved by cell bleeding, nutrient limitation and/or temperature reduction. In most perfusion cultures nutrient supply and waste removal will allow for constant cell growth and productivity and cell bleeding is required to maintain a constant viable cell density or to maintain the cells in steady state. A typical viable cell density at steady state is 20 to 50e6 cells/ml. The viable cell density may vary depending on the perfusion rate. A higher cell density can be reached by increasing the perfusion rate or by optimizing the medium for use with perfusion. At a very high viable cell density perfusion cultures become difficult to control within a bioreactor.

The term "cell bleed" and "cell bleeding" are used interchangeably and refer to the removal of cells and medium from the bioreactor in order to maintain a constant, sustainable viable cell density within the bioreactor. The constant, sustainable viable cell density may also be referred to as target cell density. This cell bleed may be done using a dip tube and a peristaltic pump at a defined flow rate. The tubing should have the right size with a too narrow tube being prone to cell aggregation and clogging while if too large the cells may settle. The cell bleed can be determined based on growth rate, thus viable cell density can be limited to a desired volume in a continuous manner. Alternatively, cells may be removed at a certain frequency, e.g., once a day, and replaced by media to maintain cell density within a predictable range. Ideally the cell bleed rate is equal to the growth rate to maintain a steady cell density.

Typically the product of interest removed with the cell bleed is discarded and therefore lost for the harvest. Opposite to a permeate, the cell bleed contains cells, which makes storage of the product prior to purification more difficult and can have detrimental effects on product quality. Thus, the cells would have to be removed continuously prior to storage and product purification, which would be laborious and cost inefficient. For slow growing cells the cell bleed may be about 10% of the removed fluid and for fast growing cells the cell bleed may be about 30% of the removed fluid. Thus, the product loss through the cell bleed may be about 30% of the product produced in total. The "permeate" as used herein refers to the harvest from which the cells have been separated to be retained in the culture vessel.

The term "culture" or "cell culture" is used interchangeably and refer to a cell population that is maintained in a medium under conditions suitable to allow survival and/or growth of the cell population. The present invention only relates to mammalian cell cultures. Mammalian cells may be cultured in suspension or while attached to a solid support. As will be clear to the person skilled a cell culture refers to a combination comprising the cell population and the medium in which the population is suspended.

The term "culturing" as used herein refers to a process by which mammalian cells are grown or maintained under controlled conditions and under conditions that supports growth and/or survival of the cells. The term "maintaining cells" as used herein is used interchangeably with "culturing cells". Culturing may also refer to a step of inoculating cells in a culture medium.

As used herein, the term "batch culture" is a discontinuous method where cells are grown in a fixed volume of culture media for a short period of time followed by a full harvest. Cultures grown using the batch method experience an increase in cell density until a maximum cell density is reached, followed by a decline in viable cell density as the media components are consumed and levels of metabolic by-products (such as lactate and ammonia) accumulate. Harvest typically occurs at or soon after the point when the maximum cell density is achieved (typically $5\text{-}10 \times 10^6$ cells/mL, depending on media formulation, cell line, etc.) typically around 3 to 7 days.

As used herein, the term "fed-batch culture" improves on the batch process by providing bolus or continuous media feeds to replenish those media components that have been consumed. Since fed-batch cultures receive additional nutrients throughout the culture process, they have the potential to achieve higher cell densities ($>10$ to $30 \times 10^6$ cells/ml, depending on media formulation, cell line, etc.) and increased product titers, when compared to the batch method. Unlike the batch process, a biphasic culture can be created and sustained by manipulating feeding strategies and media formulations to distinguish the period of cell proliferation to achieve a desired cell density (the growth phase) from the period of suspended or slow cell growth (the production phase). As such, fed batch cultures have the potential to achieve higher product titers compared to batch cultures. As with the batch method, metabolic by-product accumulation will lead to declining cell viability over time as these progressively accumulate within the cell culture media, which limits the duration of the production phase to about 1.5 to 3 weeks. Fed-batch cultures are discontinuous and harvest typically occurs when metabolic by-product levels or the culture viability reach predetermined levels.

The term "polypeptide" or "protein" is used interchangeably herein with "amino acid residue sequences" and refers to a polymer of amino acids. These terms also include proteins that are post-translationally modified through reactions that include, but are not limited to, glycosylation, acetylation, phosphorylation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with the same properties. The terms also apply to amino acid polymers in which one or more amino acid residue is an analog or mimetic of a corresponding naturally occurring amino acid. The term "polypeptide" typically refers to a sequence with more than 10 amino acids and the term "peptide" to sequences with up to 10 amino acids in length.

The term "heterologous protein" as used herein refers to a polypeptide derived from a different organism or a different species from the host cell. The heterologous protein is coded for by a heterologous polynucleotide that is experimentally put into the host cell that does not naturally express that protein. A heterologous polynucleotide may also be referred to as transgene. Thus, it may be a gene or open reading frame (ORF) coding for a heterologous protein. The term "heterologous" when used with reference to a protein may also indicate that the protein comprises amino acid sequences that are not found in the same relationship to each other or the same length in nature. Thus, it also encompasses recombinant proteins. Heterologous may also refer to a polynucleotide sequence, such as a gene or transgene, or a portion thereof, being inserted into the mammalian cell's genome in a location in which it is not typically found. In the present invention the heterologous protein is preferably a therapeutic protein.

The term "medium", "cell culture medium" and "culture medium" are used interchangeably herein and refer to a solution of nutrients that nourish cells, particularly mammalian cells. Cell culture media formulations are well known in the art. Typically a cell culture medium provides essential and non-essential amino acids, vitamins, energy sources, lipids and trace elements required by the cell for minimal growth and/or survival, as well as buffers, and salts. A culture medium may also contain supplementary components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source; as described herein. In certain embodiments, a medium is advantageously formulated to a pH and salt concentration optimal for cell survival and proliferation. The medium according to the invention is a perfusion culture medium that is added after the beginning of the cell culture. In certain embodiments, the cell culture medium is a mixture of a starting nutrient solution (basal medium or inoculation medium) and any culture medium that is added after the beginning of the cell culture.

The term "serum-free" as used herein refers to a cell culture medium that does not contain animal or human serum, such as fetal bovine serum. Preferably serum-free medium is free of proteins isolated from any animal or human derived serum. Various tissue culture media, including defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoys 5A Medium, Leibovitz's L-15 Medium, and serum-free media such as EX-CELL™ 300 Series (JRH Biosciences, Lenexa, Kans.), among others. Serum-free versions of such culture media are also available. Cell culture media may be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters.

The term "protein-free" as used herein refers to a cell culture medium that does not contain any protein. Thus, it is devoid of proteins isolated from an animal or human, derived from serum or recombinantly produced proteins, such as recombinant proteins produced in mammalian, bacterial, insect or yeast cells. A protein-free medium may contain single recombinant proteins, such as insulin or insulin-like growth factor, but only if this addition is explicitly stated.

As used herein the term "chemically defined" refers to a culture medium, which is serum-free and which does not contain any hydrolysates, such as protein hydrolysates derived from yeast, plants or animals. Preferably a chemically defined medium is also protein-free or contains only selected recombinantly produced (not animal derived) proteins, such as insulin or insulin-like growth factor. Chemically defined medium consist of a mixture of characterized and purified substances. An example of a chemically defined medium is for example CD-CHO medium from Invitrogen (Carlsbad, Calif., US).

The term "suspension cells" or "non-adherent cells" as used herein relates to cells that are cultured in suspension in liquid medium. Adhesive cells such as CHO cells may be adapted to be grown in suspension and thereby lose their ability to attach to the surface of the vessel or tissue culture dish.

As used herein, the term "bioreactor" means any vessel useful for the growth of a cell culture. A bioreactor can be of any size as long as it is useful for the culturing of cells; typically, a bioreactor is sized appropriate to the volume of cell culture being grown inside of it. Typically, a bioreactor will be at least 1 liter and may be 2, 5, 10, 50, 100, 200, 250, 500, 1,000, 1,500, 2,000, 2,500, 5,000, 8,000, 10,000, 12,000 liters or more, or any volume in between. The internal conditions of the bioreactor, including, but not limited to pH and temperature, can be controlled during the culturing period. Those of ordinary skill in the art will be aware of, and will be able to select, suitable bioreactors for use in practicing the present invention based on the relevant considerations. The cell cultures used in the methods of the present invention can be grown in any bioreactor suitable for perfusion culture.

As used herein, "cell density" refers to the number of cells in a given volume of culture medium. "Viable cell density" refers to the number of live cells in a given volume of culture medium, as determined by standard viability assays (such as trypan blue dye exclusion method).

As used herein, the term "cell viability" means the ability of cells in culture to survive under a given set of culture conditions or experimental variations. The term as used herein also refers to that portion of cells which are alive at a particular time in relation to the total number of cells, living and dead, in the culture at that time.

As used herein, the term "titer" means the total amount of a polypeptide or protein of interest (which may be a naturally occurring or recombinant protein of interest) produced by a cell culture in a given amount of medium volume. Titer can be expressed in units of milligrams or micrograms of polypeptide or protein per milliliter (or other measure of volume) of medium.

As used herein, the term "yield" refers to the amount of heterologous protein produced in perfusion culture over a certain period of time. The "total yield" refers to the amount of heterologous protein produced in perfusion culture over the entire run.

The term "reduction", "reduced" or "reduce", as used herein, generally means a decrease by at least 10% as compared to a reference level, for example a decrease by at least about 20%, or at least about 30%, or at least about 40%, or at least about 50%, or at least about 60%, or at least about 70%, or at least about 75%, or at least about 80%, or at least about 90% or up to and including a 100% decrease, or any integer decrease between 10-100% as compared to a control mammalian cell culture, which is cultured under the same conditions using the same serum-free perfusion medium comprising a potassium ions lower than the concentrations used in the perfusion medium of the invention.

The term "enhancement", "enhanced", "enhanced", "increase" or "increased", as used herein, generally means an increase by at least 10% as compared to a control cell, for example an increase by at least about 20%, or at least about 30%, or at least about 40%, or at least about 50%, or at least about 75%, or at least about 80%, or at least about 90%, or at least about 100%, or at least about 200%, or at least about 300%, or any integer decrease between 10-300% as compared to a mammalian cell culture, which is cultured under the same conditions using the same serum-free perfusion medium comprising a potassium ions lower than the concentrations used in the perfusion medium of the invention.

As used herein, a "control cell culture" or "control mammalian cell culture" is a cell which is the same as the cell culture to which it is compared to, except that the perfusion medium does not have the potassium concentration of the perfusion medium of the invention, preferably the control perfusion medium does not have the potassium concentration of the perfusion medium of the invention and does not have the molar Na:K ratio of the perfusion medium of the invention.

The term "mammalian cells" as used herein are cells lines suitable for the production of a heterologous protein, preferably a therapeutic protein, more preferably a secreted recombinant therapeutic protein. Preferred mammalian cells according to the invention are rodent cells such as hamster cells. The mammalian cells are isolated cells or cell lines. The mammalian cells are preferably transformed and/or immortalized cell lines. They are adapted to serial passages in cell culture and do not include primary non-transformed cells or cells that are part of an organ structure. Preferred mammalian cells are BHK21, BHK TK$^-$, CHO, CHO-K1, CHO-S cells, CHO-DXB11 (also referred to as CHO-DUKX or DuxB11), and CHO-DG44 cells or the derivatives/progenies of any of such cell line. Particularly preferred are CHO-DG44, CHO-K1 and BHK21, and even more preferred are CHO-DG44 and CHO-K1 cells. Most preferred are CHO-DG44 cells. Glutamine synthetase (GS)-deficient derivatives of the mammalian cell, particularly of the CHO-DG44 and CHO-K1 cell are also encompassed. The mammalian cell may further comprise one or more expression cassette(s) encoding a heterologous protein, preferably a recombinant secreted therapeutic protein. The mammalian cells may also be murine cells such as murine myeloma cells, such as NS0 and Sp2/0 cells or the derivatives/progenies of any of such cell line. However, derivatives/progenies of those cells, other mammalian cells, including but not limited to human, mice, rat, monkey, and rodent cell lines, can also be used in the present invention, particularly for the production of biopharmaceutical proteins.

The term "growth phase" as used herein refers to the phase of cell culture where the cells proliferate exponentially and viable cell density in the bioreactor is increasing. Cells in culture usually proliferate following a standard growth pattern. The first phase of growth after the culture is seeded is the lag phase, which is a period of slow growth when the cells are adapting to the culture environment and preparing for fast growth. The lag phase is followed by the growth phase (also referred to as log phase or logarithmic phase), a period where the cells proliferate exponentially and consume the nutrients of the growth medium. The production phase starts once the target cell density is reached and/or harvest is started. A typical target cell density is in the range of $10 \times 10^6$ cells/ml to about $120 \times 10^6$ cells/ml, but may be even higher. Thus, the target cell density according to the present invention is at least $10 \times 10^6$ cells/ml, at least $20 \times 10^6$ cells/ml, at least $30 \times 10^6$ cells/ml, at least $40 \times 10^6$ cells/ml or at least $50 \times 10^6$ cells/ml. Most preferably the target cell density is about 30 to about $50 \times 10^6$ cells/ml. Viable cell density is dependent on the perfusion rate and can be maintained at a constant level using regular or continuous cell bleeds.

The term "growth-arrest" as used herein refers to cells that are stopped from increasing in number, i.e., from cell division. The cell cycle comprises the interphase and the mitotic phase. The interphase consists of three phases: DNA replication is confined to S phase; $G_1$ is the gap between M phase and S phase, while $G_2$ is the gap between S phase and M phase. In M phase, the nucleus and then the cytoplasm divide. In the absence of a mitogenic signal to proliferate or in the presence of compounds that induce growth arrest the cell cycle arrests. The cells may partly disassemble their cell-cycle control system and exit from the cycle to a specialized, non-dividing state called $G_0$.

The term "about" as used herein refers to a variation around the actual value provided and encompasses plus and minus 10% of the value.

Methods of Culturing Cells Using Perfusion Culture

For the purposes of understanding, yet without limitation, it will be appreciated by the skilled practitioner that cell cultures and culturing runs for protein production can include three general types; namely, perfusion culture, batch culture and fed-batch culture. In a perfusion culture, for example, fresh culture medium supplement is provided to the cells during the culturing period, while old culture medium is removed daily and the product is harvested, for example, daily or continuously. In perfusion culture, perfusion medium can be added daily and can be added continuously, i.e., as a drip or infusion. For perfusion culturing, the cells can remain in culture as long as is desired, so long as the cells remain alive and the environmental and culturing conditions are maintained. Since the cells grow continuously, it is typically required to remove cells during the run in order to maintain a constant viable cell density, which is referred to as cell bleed. The cell bleed contains product in the culture medium removed with the cells, which is typically discarded and hence wasted. Thus, maintaining the viable cell density during production phase without or with only minimal cell bleeding is advantageous and increases the total yield per run.

In batch culture, cells are initially cultured in medium and this medium is not removed, replaced, or supplemented, i.e., the cells are not "fed" with new medium, during or before the end of the culturing run. The desired product is harvested at the end of the culturing run.

For fed-batch cultures, the culturing run time is increased by supplementing the culture medium one or more times daily (or continuously) with fresh medium during the run, i.e., the cells are "fed" with new medium ("feeding medium") during the culturing period. Fed-batch cultures can include the various feeding regimens and times as described above, for example, daily, every other day, every two days, etc., more than once per day, or less than once per day, and so on. Further, fed-batch cultures can be fed continuously with feeding medium. The desired product is then harvested at the end of the culturing/production run.

According to the present invention mammalian cells are cultured in perfusion culture. During heterologous protein production it is desirable to have a controlled system where cells are grown to a desired viable cell density and then the cells are switched to a growth-arrested, high productivity state where the cells use energy and substrates to produce the heterologous protein of interest rather than cell growth and cell division. Methods for accomplishing this goal, such as temperature shifts and amino acid starvation, are not always successful and can have undesirable effects on product quality. As described herein viable cell density during production phase can be maintained at a desirable level by performing a regular cell bleed. However, this results in discarding heterologous protein of interest. Cell growth-arrest during production phase results in a reduced need for a cell bleed and may even maintain cells in a more productive state.

Provided herein is a method of culturing mammalian cells expressing a heterologous protein in a perfusion cell culture comprising: (a) inoculating mammalian cells expressing a heterologous protein in a serum-free culture medium; (b) culturing the mammalian cells during growth phase by perfusion with a serum-free perfusion medium; and (c) culturing the mammalian cells during production phase by perfusion with a serum-free perfusion medium comprising potassium ions at a concentration of 30 mM to 250 mM and a molar ratio of sodium to potassium ions of less than 1, wherein step (b) is optional.

Also provided herein is a method of reducing cell bleeding in a perfusion cell culture and/or increasing protein production in a perfusion cell culture expressing a heterologous protein comprising: (a) inoculating mammalian cells expressing a heterologous protein in a serum-free culture medium; (b) culturing the mammalian cells during growth phase by perfusion with a serum-free perfusion medium; and (c) culturing the mammalian cells during production phase by perfusion with a serum-free perfusion medium comprising potassium ions at a concentration of 30 mM to 250 mM and a molar ratio of sodium to potassium ions of less than 1, wherein step (b) is optional.

It is also encompassed by the invention that the perfusion culture is inoculated with a very high cell density and perfusion is started immediately or shortly after inoculation of mammalian cells expressing a heterologous protein in a serum-free culture medium. Further, step (b) culturing the mammalian cells during growth phase by perfusion with a serum-free perfusion medium may be optional so that the mammalian cells are immediately cultured according to step (c) during production phase by perfusion with a serum-free by perfusion with a serum-free perfusion medium comprising potassium ions at a concentration of 30 mM to 250 mM and a molar ratio of sodium to potassium ions of less than 1.

Thus, also provided herein is a method of culturing mammalian cells expressing a heterologous protein and/or reducing cell bleeding in a perfusion cell culture and/or increasing protein production in a perfusion cell culture expressing a heterologous protein comprising: (a) inoculating mammalian cells expressing a heterologous protein in a serum-free culture medium; (b) optionally culturing the mammalian cells during growth phase by perfusion with a serum-free perfusion medium; and (c) culturing the mammalian cells during production phase by perfusion with a serum-free perfusion medium comprising potassium ions at a concentration of 30 mM to 250 mM and a molar ratio of sodium to potassium ions of less than 1. Increasing the protein production encompasses an increased protein product yield over the perfusion run or over a certain period of time. It also encompasses an increased specific protein production per cell, or both.

According to the methods of the invention, culturing the mammalian cells in step (a) may be limited to inoculating mammalian cells expressing a heterologous protein in a serum-free medium and hence does not need to include an actual culturing step prior to the start of perfusion. Further according to the methods of the invention, culturing the mammalian cells during production phase by perfusion includes maintaining the mammalian cells during production phase by perfusion at a constant viable cell density.

The production phase starts once the target cell density is reached. Preferably step (c) is started once the target cell density is reached. It may be started at a cell density in the range of $10\times10^6$ cells/ml to about $120\times10^6$ cells/ml or even higher. Preferably step (c) is initiated at a cell density of at least $10\times10^6$ cells/ml, at least $20\times10^6$ cells/ml, at least $30\times10^6$ cells/ml, at least $40\times10^6$ cells/ml or at least $50\times10^6$ cells/ml. Most preferably step (c) is initiated at a cell density of about 30 to about $50\times10^6$ cells/ml.

The methods of the invention may further comprise that in step (c) the cell density is maintained by cell bleeding. The cell density referred to in this context is the viable cell density, which may be determined by any method known in the art. For example the calculation governing the cell bleed rate may be based on maintaining the INCYTE or FUTURA biomass capacitance probe value (Hamilton company, Aber instruments) which corresponded to the target VCD, or a daily cell and viability count can be taken off-line via any cell counting device, such as haemocytometer, VI-CELL (Beckman Coulter), CEDEX HI RES (Roche), or VIA-COUNT assay (EMD Millipore GUAVA EASYCYTE). Using the methods of the present invention the cell bleeding is reduced compared to a control perfusion cell culture, wherein a control perfusion cell culture is a perfusion cell culture that is cultured under the same conditions using the same serum-free perfusion medium without the potassium concentration and the ratio of sodium to potassium ions according to the invention. More specifically the cell bleeding is reduced compared to a control perfusion cell culture, wherein a control perfusion cell culture is a perfusion cell culture that is cultured under the same conditions using the same serum-free perfusion medium comprising potassium ions at a concentration of less than 30 mM and a molar ratio of sodium to potassium of more than 2.

A preferred potassium ion concentration in the serum-free perfusion medium of the invention is about 40 mM to about 200 mM, preferably about 60 mM to about 150 mM and more preferably about 80 mM to about 100 mM. In some embodiments the molar ratio of sodium to potassium is between about 0.9 and 0.1, between about 0.8 and 0.2, between about 0.7 and 0.2, preferably between about 0.6 and 0.3 and more preferably between about 0.5 and 0.4. Examples of suitable potassium concentrations and Na:K ratios are about 40 mM to about 200 mM and a molar Na:K ratio of about 0.1 to 0.9, about 40 mM to about 200 mM and a molar Na:K ratio of about 0.2 to 0.8; about 40 mM to about 200 mM and a molar Na:K ratio of about 0.2 to 0.7; 40 mM to about 200 mM and a molar Na:K ratio of about 0.3 to 0.6; 40 mM to about 200 mM and a molar Na:K ratio of about 0.4 to 0.5; about 60 mM to about 150 mM and a molar Na:K ratio of about 0.1 to 0.9; about 60 mM to about 150 mM and a molar Na:K ratio of about 0.2 to 0.8; about 60 mM to about 150 mM and a molar Na:K ratio of about 0.2 to 0.7; about 60 mM to about 150 mM and a molar Na:K ratio of about 0.3 to 0.6; about 60 mM to about 150 mM and a molar Na:K ratio of about 0.4 to 0.5; about 80 mM to about 100 mM and a molar Na:K ratio of about 0.1 to 0.9, about 80 mM to about 100 mM and a molar Na:K ratio of about 0.2 to 0.8; about 80 mM to about 100 mM and a molar Na:K ratio of about 0.2 to 0.7; about 80 mM to about 100 mM and a molar Na:K ratio of about 0.3 to 0.6; about 80 mM to about 100 mM and a molar Na:K ratio of about 0.4 to 0.5. Particularly preferred is a potassium concentration of about 60 mM to about 150 mM and a molar Na:K ratio of about 0.6 to 0.3, even more preferred is a potassium concentration of about 60 mM to about 150 mM and a molar Na:K ratio of about 0.5 and 0.4 and even more preferred is a potassium concentration of about 80 mM to about 100 mM and a molar Na:K ratio of about 0.5 and 0.4. The potassium concentrations according to the invention together with the molar Na:K ratio according to the invention lead to a $G_0/G_1$ cell cycle arrest. Additionally the potassium concentrations according to the invention together with the molar Na:K ratio according to the invention lead to an increased cell specific productivity (qp). Thus the high potassium concentration according to the invention and the resulting low sodium concentration of the invention seem to act synergistically. Without being bound by theory it seems that the potassium concentrations according to the invention are required for the $G_0/G_1$ cell cycle arrest and the simultaneous reduction in sodium ions and hence a reduced molar Na:K ratio promotes the increased cell specific productivity.

The potassium ion may be provided as one or more potassium salt. In a preferred embodiment the one or more potassium salt is selected from the group consisting of potassium bicarbonate, potassium chloride, potassium hydroxide, L-tyrosine dipotassium salt, potassium phosphate dibasic, potassium phosphate monobasic, potassium selenite, potassium pyruvic acid, potassium glutathione, potassium D-gluconate, potassium succinate and potassium ascorbate. More preferably the potassium salt is potassium bicarbonate, potassium chloride, potassium hydroxide, L-tyrosine dipotassium salt, potassium phosphate dibasic and potassium phosphate monobasic. Preferably the osmolarity of a medium is not changed by the addition of the potassium salt. This may be achieved by replacing a sodium salt with the corresponding potassium salt. The skilled person would therefore understand that any sodium salt typically used in a cell culture medium is a preferred salt to be used as the corresponding potassium salt. Preferably the potassium salt substitutes the corresponding sodium salt in the serum-free perfusion medium of step (b).

A preferred sodium ion concentration in the serum-free perfusion medium of the invention is less than 100 mM, more preferably less than 60, even more preferably 10-50 mM. The sodium ion may be provided as one or more sodium salt. In a preferred embodiment the one or more sodium salt is selected from the group consisting of sodium bicarbonate, sodium chloride, sodium hydroxide, L-tyrosine di sodium salt, sodium phosphate dibasic, sodium phosphate monobasic, sodium selenite, sodium pyruvic acid, sodium glutathione, sodium D-gluconate, sodium succinate and sodium ascorbate. More preferably the sodium salt is sodium bicarbonate, sodium chloride, sodium hydroxide, L-tyrosine disodium salt, sodium phosphate dibasic, sodium phosphate monobasic.

For the same reason and to allow growth during growth phase, the potassium ion concentration and the molar Na:K ratio of the serum-free perfusion medium of the invention should be avoided in the inoculation medium and during growth phase. Thus, the serum-free culture medium of step (a) and the serum-free perfusion medium of step (b) should comprise potassium at a concentration lower than the potassium ion concentration of the serum-free perfusion medium of the invention and a molar Na:K ratio higher than the molar Na:K ratio of the serum-free perfusion medium of the invention. Preferably the serum-free culture medium of step (a) and the serum-free perfusion medium of step (b) comprise a potassium concentration of less than 30 mM. More preferably the serum-free culture medium of step (a) and the serum-free perfusion medium of step (b) comprise a potassium concentration of less than 30 mM. and a molar ratio of sodium to potassium of more than 1, preferably of more than 2.

The osmolarity of the serum-free perfusion medium of the invention should be in the range of between 300 and 1400 mOsmol/kg, preferably between 300 and 500 mOsmol/kg, more preferably between 330 and 450 mOsmol/kg and even more preferably between 360 and 390 mOsmol/kg. Wherein the osmolarity is provided as mOsmol/kg water.

The serum-free perfusion medium of the invention and the serum-free perfusion medium used in the methods of the invention may be chemically defined and/or hydrolysate-free. Hydrolysate-free means that the medium does not contain protein hydrolysates from animal, plant (soybean, potato, rice), yeast or other sources. Typically a chemically defined medium is hydrolysate-free. In any case the serum-free perfusion medium should be free of compounds derived from animal sources, particularly proteins or peptides derived and isolated from an animal (this does not include recombinant proteins produced by the cell culture). Preferably the serum-free perfusion medium is protein-free or protein-free except for recombinant insulin and/or insulin-like growth factor. More preferably the serum-free perfusion medium is chemically defined and protein-free or protein-free except for recombinant insulin and/or insulin-like growth factor. This also applies to the serum-free culture medium of step (a) and the serum-free perfusion medium of step (b).

A perfusion culture typically starts with an inoculation culture as batch culture. Perfusion may start immediately or after one or more days. Typically perfusion starts on or after day 2 of the cell culture. In one embodiment the perfusion in step (b) begins on or after day 2 of the cell culture. Once the target cell density is reached growth arrest is induced by increasing the potassium ion concentration and simultaneously reducing the molar Na:K ratio in the cell culture to obtain the concentration and the ratio of the serum-free perfusion medium of the invention in the cell culture. During production phase the mammalian cells are cultured by perfusion with a serum-free perfusion medium comprising potassium ions at a concentration of 30 mM to 250 mM and a molar ratio of sodium to potassium ions of less than 1.

Typically the mammalian cell culture according to the invention comprises continuous perfusion of the cell culture. The perfusion rate may increase after perfusion has started. Typically a higher perfusion rate supports a higher viable cell density and therefore allows for a higher target cell density. The perfusion rate may increase from less than or equal to 0.5 vessel volumes per day to 5 vessel volumes per day. Preferably the perfusion rate increases from less than or equal to 0.5 vessel volumes per day to 2 vessel volumes per day.

The methods of the present invention further comprise harvesting the heterologous protein from the perfusion cell culture. This is preferably done continuously from the permeate, which is the supernatant produced after cells have been recovered by a cell retention device. Due to the lower product residence time of the product proteins in the cell culture inside the perfusion bioreactor compared to fed-batch, the exposure to proteases, sialidases and other degrading proteins is minimized, which may result in better product quality of heterologous proteins produced in perfusion culture.

According to the methods of the present invention any cell perfusion bioreactor and cell retention device may be used for perfusion culture. The bioreactors used for perfusion are not very different from those used for batch/fed-batch cultures, except that they are more compact in size and are connected to a cell retention device. The methods for retaining cells inside the bioreactor are primarily determined by whether the cells are growing attached to surfaces or growing in either single cell suspension or cell aggregates. While most mammalian cells historically were grown attached to a surface or a matrix (heterogenous cultures), efforts have been made to adapt many industrial mammalian cell lines to grow in suspension (homogenous cultures), mainly because suspension cultures are easier to scale-up. Thus, the cells used in the methods of the invention are preferably grown in suspension. Without being limited thereto, exemplary retention systems for cells grown in suspension are spin filter, external filtration such as tangential flow filtration (TFF), alternating tangential flow (ATF) system, cell sedimentation (vertical sedimentation and inclined sedimentation), centrifugation, ultrasonic separation and hydrocyclones. Perfusion systems can be categorized into two categories, filtration based systems, such as spin filters, external filtration and ATF, and open perfusion systems, such as gravitational settlers, centrifuges, ultrasonic separation devices and hydroclones. Filtration-based systems show a high degree of cell retention and it does not change with the flow rate. However, the filters may clog and hence the cultivation run is limited in length or the filters need to be exchanged. An example for an ATF system is the ATF 2 system from Repligen and an example for a TFF system is the TFF system from Levitronix using a centrifugal pump. A cross-flow filter, such as a hollow fiber (HF) or a flat plate filter may be used with ATF and TFF systems. Specifically a hollow fiber, made of modified polyethersulfone (mPES), polyethersulfone (PES), or polysulfone (PE), can be used with ATF and TFF systems. Pore sizes of the HF can range from several hundred kDa to 15 µM. Open perfusion systems do not clog and hence could at least theoretically be operated indefinitely. However, the degree of cell retention is reduced at higher perfusion rates. Currently there are four systems that can be used at industrial scale, alternating tangential filters (ATF), gravitational (particularly inclined settlers), tangential flow filtration (TFF) and centrifuges. Cell retention devices suitable for heterogenous or homogenous cultures are described in more detail by Kompala and Ozturk (Cell Culture Technology for Pharmaceutical and Cell-Based Therapies, (2006), Taylor & Francis Group, LLC, pages 387-416). The perfusion culture is not a true steady state process, with the total and viable cell concentration reaching a steady state only when a cell bleed stream is removed from the bioreactor.

Physical parameters such as pH, dissolved oxygen and temperature in a perfusion bioreactor should be monitored on-line and controlled in real time. Determination of cell density, viability, metabolite, and product concentrations may be performed using off-line or on-line sampling. When the perfusion operation starts with continuous harvest and feeding the perfusion rate typically refers to the harvest flow rate, which may be manually set to a desired value. For example, a weight control for the bioreactor may activate the feed pump so that a constant volume in the bioreactor can be maintained. Alternatively, a level control can be achieved by pumping out culture volume above a predetermined level. The perfusion rate in the bioreactor must be adjusted to deliver sufficient nutrients to the cells. As the cell density increases in the bioreactor, the perfusion rate must be increased.

Perfusion rate may be controlled, e.g., using cell density measurements, pH measurements, oxygen consumption or metabolite measurements. Cell density is the most important measurement used for perfusion rate adjustments. Depending on how the cell density measurements are conducted, perfusion rates can be adjusted daily or in real time. Several on-line probes have been developed for the estimation of cell density and are known to the person skilled in the art, such as a capacitance probe, e.g., an INCYTE probe (Hamilton Company) or a FUTURA probe (Aber instruments). These cell density probes can also be used to control the cell density at a desired set point by removing excess cells from the bioreactor, i.e., the cell bleed. Thus, the cell bleed is determined by the specific growth rate of the mammalian cells in culture. The cell bleed is typically not harvested and therefore considered as waste.

In yet another aspect a use of the serum-free perfusion medium of the invention for culturing mammalian cells in a perfusion culture during production phase or for reducing the total cell bleed volume in a perfusion culture is provided. Alternatively, a use of the serum-free perfusion medium of the invention for increasing protein production in a perfusion cell culture is provided. The use of the medium is as disclosed for the serum-free perfusion medium (of step (c)) used in the methods of the inventions.

The heterologous protein produced by the methods and uses of the present invention may be any secreted protein, preferably it is a therapeutic protein. Since most therapeutic proteins are recombinant therapeutic proteins, it is most preferably a recombinant therapeutic protein. Examples for therapeutic proteins are without being limited thereto antibodies, fusion proteins, cytokines and growth factor.

The therapeutic protein produced in the mammalian cells according to the methods of the invention includes, but is not limited to an antibodies or a fusion protein, such as a Fc-fusion proteins. Other secreted recombinant therapeutic proteins can be for example enzymes, cytokines, lymphokines, adhesion molecules, receptors and derivatives or fragments thereof, and any other polypeptides and scaffolds that can serve as agonists or antagonists and/or have therapeutic or diagnostic use.

Other recombinant proteins of interest are for example, without being limited thereto: insulin, insulin-like growth factor, hGH, tPA, cytokines, such as interleukins (IL), e.g. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosis factor (TNF), such as TNF alpha and TNF beta, TNF gamma, TRAIL; G-CSF, GM-CSF, M-CSF, MCP-1, and VEGF. Also included is the production of erythropoietin or any other hormone growth factors and any other polypeptides that can serve as agonists or antagonists and/or have therapeutic or diagnostic use.

A preferred therapeutic protein is an antibody or a fragment or derivative thereof, more preferably an IgG1 antibody. Thus, the invention can be advantageously used for production of antibodies such as monoclonal antibodies, multi-specific antibodies, or fragments thereof, preferably of monoclonal antibodies, bi-specific antibodies or fragments thereof. Exemplary antibodies within the scope of the present invention include but are not limited to anti-CD2, anti-CD3, anti-CD20, anti-CD22, anti-CD30, anti-CD33, anti-CD37, anti-CD40, anti-CD44, anti-CD44v6, anti-CD49d, anti-CD52, anti-EGFR1 (HER1), anti-EGFR2 (HER2), anti-GD3, anti-IGF, anti-VEGF, anti-TNFalpha, anti-IL2, anti-IL-5R or anti-IgE antibodies, and are preferably selected from the group consisting of anti-CD20, anti-CD33, anti-CD37, anti-CD40, anti-CD44, anti-CD52, anti-HER2/neu (erbB2), anti-EGFR, anti-IGF, anti-VEGF, anti-TNFalpha, anti-IL2 and anti-IgE antibodies.

Antibody fragments include e.g. "Fab fragments" (Fragment antigen-binding=Fab). Fab fragments consist of the variable regions of both chains, which are held together by the adjacent constant region. These may be formed by protease digestion, e.g. with papain, from conventional antibodies, but similarly Fab fragments may also be produced by genetic engineering. Further antibody fragments include F(ab')2 fragments, which may be prepared by proteolytic cleavage with pepsin.

Using genetic engineering methods it is possible to produce shortened antibody fragments which consist only of the variable regions of the heavy (VH) and of the light chain (VL). These are referred to as Fv fragments (Fragment variable=fragment of the variable part). Since these Fv-fragments lack the covalent bonding of the two chains by the cysteines of the constant chains, the Fv fragments are often stabilized. It is advantageous to link the variable regions of the heavy and of the light chain by a short peptide fragment, e.g. of 10 to 30 amino acids, preferably 15 amino acids. In this way a single peptide strand is obtained consisting of VH and VL, linked by a peptide linker. An antibody protein of this kind is known as a single-chain-Fv (scFv). Examples of scFv-antibody proteins are known to the person skilled in the art.

Preferred therapeutic antibodies according to the invention are bispecific antibodies. Bispecific antibodies typically combine antigen-binding specificities for target cells (e.g., malignant B cells) and effector cells (e.g., T cells, NK cells or macrophages) in one molecule. Exemplary bispecific antibodies, without being limited thereto are diabodies, BiTE (Bi-specific T-cell Engager) formats and DART (Dual-Affinity Re-Targeting) formats. The diabody format separates cognate variable domains of heavy and light chains of the two antigen binding specificities on two separate polypeptide chains, with the two polypeptide chains being associated non-covalently. The DART format is based on the diabody format, but it provides additional stabilization through a C-terminal disulfide bridge.

Another preferred therapeutic protein is a fusion protein, such as a Fc-fusion protein. Thus, the invention can be advantageously used for production of fusion proteins, such as Fc-fusion proteins. Furthermore, the method of increasing protein producing according to the invention can be advantageously used for production of fusion proteins, such as Fc-fusion proteins.

The effector part of the fusion protein can be the complete sequence or any part of the sequence of a natural or modified heterologous protein or a composition of complete sequences or any part of the sequence of a natural or modified heterologous protein. The immunoglobulin constant domain sequences may be obtained from any immunoglobulin subtypes, such as IgG1, IgG2, IgG3, IgG4, IgA1 or IgA2 subtypes or classes such as IgA, IgE, IgD or IgM. Preferentially they are derived from human immunoglobulin, more preferred from human IgG and even more preferred from human IgG1 and IgG2 Non-limiting examples of Fc-fusion proteins are MCP1-Fc, ICAM-Fc, EPO-Fc and scFv fragments or the like coupled to the CH2 domain of the heavy chain immunoglobulin constant region comprising the N-linked glycosylation site. Fc-fusion proteins can be constructed by genetic engineering approaches by introducing the CH2 domain of the heavy chain immunoglobulin constant region comprising the N-linked glycosylation site into another expression construct comprising for example other immunoglobulin domains, enzymatically active protein portions, or effector domains. Thus, an Fc-fusion protein according to the present invention comprises also a single chain Fv fragment linked to the CH2 domain of the heavy chain immunoglobulin constant region comprising e.g. the N-linked glycosylation site.

In a further aspect a method of producing a therapeutic protein is provided using the methods of the invention and optionally further comprising a step of purifying and formulating the therapeutic protein into a pharmaceutically acceptable formulation.

The therapeutic protein, especially the antibody, antibody fragment or Fc-fusion protein is preferably recovered/isolated from the culture medium as a secreted polypeptide. It is necessary to purify the therapeutic protein from other recombinant proteins and host cell proteins to obtain substantially homogenous preparations of the therapeutic protein. As a first step, cells and/or particulate cell debris are removed from the culture medium. Further, the therapeutic protein is purified from contaminant soluble proteins, polypeptides and nucleic acids, for example, by fractionation on immunoaffinity or ion-exchange columns, ethanol precipitation, reverse phase HPLC, Sephadex chromatography, and chromatography on silica or on a cation exchange resin such as DEAE. Methods for purifying a heterologous protein expressed by mammalian cells are known in the art.

In one embodiment the heterologous protein expressed using the methods of the invention is encoded by one or more expression cassette(s) comprising a heterologous polynucleotide coding for the heterologous protein. The heterologous protein may be placed under the control of an amplifiable genetic selection marker, such as dihydrofolate reductase (DHFR), glutamine synthetase (GS). The amplifiable selection marker gene can be on the same expression vector as the heterologous protein expression cassette. Alternatively, the amplifiable selection marker gene and the heterologous protein expression cassette can be on different expression vectors, but integrate in close proximity into the host cell's genome. Two or more vectors that are co-transfected simultaneously, for example, often integrate in close proximity into the host cell's genome. Amplification of the genetic region containing the secreted therapeutic protein expression cassette is then mediated by adding the amplification agent (e.g., MTX for DHFR or MSX for GS) into the cultivation medium.

Sufficiently high stable levels of a heterologous protein expressed by a mammalian cell may also be achieved, e.g., by cloning multiple copies of the heterologous protein encoding-polynucleotide into an expression vector. Cloning multiple copies of the heterologous protein-encoding polynucleotide into an expression vector and amplifying the heterologous protein expression cassette as described above may further be combined.

Mammalian Cell Lines

Mammalian cells as used herein are mammalian cells lines suitable for the production of a secreted recombinant therapeutic protein and may hence also be referred to as "host cells". Preferred mammalian cells according to the invention are rodent cells such as hamster cells. The mammalian cells are isolated cells or cell lines. The mammalian cells are preferably transformed and/or immortalized cell lines. They are adapted to serial passages in cell culture and do not include primary non-transformed cells or cells that are part of an organ structure. Preferred mammalian cells are BHK21, BHK TK-, CHO, CHO-K1, CHO-DXB11 (also referred to as CHO-DUKX or DuxB11), a CHO-S cell and CHO-DG44 cells or the derivatives/progenies of any of such cell line. Particularly preferred are CHO cells, such as CHO-DG44, CHO-K1 and BHK21, and even more preferred are CHO-DG44 and CHO-K1 cells. Most preferred are CHO-DG44 cells. Glutamine synthetase (GS)-deficient derivatives of the mammalian cell, particularly of the CHO-DG44 and CHO-K1 cell are also encompassed. In one embodiment of the invention the mammalian cell is a Chinese hamster ovary (CHO) cell, preferably a CHO-DG44 cell, a CHO-K1 cell, a CHO DXB11 cell, a CHO-S cell, a CHO GS deficient cell or a derivative thereof.

The mammalian cell may further comprise one or more expression cassette(s) encoding a heterologous protein, such as a therapeutic protein, preferably a recombinant secreted therapeutic protein. The host cells may also be murine cells such as murine myeloma cells, such as NS0 and Sp2/0 cells or the derivatives/progenies of any of such cell line. Non-limiting examples of mammalian cells which can be used in the meaning of this invention are also summarized in Table 1. However, derivatives/progenies of those cells, other mammalian cells, including but not limited to human, mice, rat, monkey, and rodent cell lines, can also be used in the present invention, particularly for the production of biopharmaceutical proteins.

TABLE 1

Mammalian production cell lines

| Cell line | Order Number |
| --- | --- |
| NS0 | ECACC No. 85110503 |
| Sp2/0-Ag14 | ATCC CRL-1581 |
| BHK21 | ATCC CCL-10 |
| BHK TK− | ECACC No. 85011423 |
| HaK | ATCC CCL-15 |
| 2254-62.2 (BHK-21 derivative) | ATCC CRL-8544 |
| CHO | ECACC No. 8505302 |
| CHO wild type | ECACC 00102307 |
| CHO-K1 | ATCC CCL-61 |
| CHO-DUKX (=CHO duk−, CHO/dhfr−,CHO-DXB11) | ATCC CRL-9096 |
| CHO-DUKX 5A-HS-MYC | ATCC CRL-9010 |
| CHO-DG44 | Urlaub G, et al., 1983. Cell. 33: 405-412. |
| CHO Pro-5 | ATCC CRL-1781 |
| CHO-S | Life Technologies A1136401; CHO-S is derived from CHO variant Tobey et al. 1962 |
| V79 | ATCC CCC-93 |
| B14AF28-G3 | ATCC CCL-14 |
| HEK 293 | ATCC CRL-1573 |
| COS-7 | ATCC CRL-1651 |
| U266 | ATCC TIB-196 |
| HuNS1 | ATCC CRL-8644 |
| CHL | ECACC No. 87111906 |
| CAP[1] | Wölfel J, et al., 2011. BMC Proc. 5 (Suppl 8): P133. |
| PER.C6 ® | Pau et al., 2001. Vaccines. 19: 2716-2721. |
| H4-II-E | ATCC CRL-1548 ECACC No. 87031301 Reuber, 1961. J. Natl. Cancer Inst. 26: 891-899. Pitot HC, et al., 1964. Natl. Cancer Inst. Monogr. 13: 229-245. |
| H4-II-E-C3 | ATCC CRL-1600 |
| H4TG | ATCC CRL-1578 |
| H4-II-E | DSM ACC3129 |
| H4-II-Es | DSM ACC3130 |

[1]CAP (CEVEC's Amniocyte Production) cells are an immortalized cell line based on primary human amniocytes. They were generated by transfection of these primary cells with a vector containing the functions E1 and pIX of adenovirus 5. CAP cells allow for competitive stable production of recombinant proteins with excellent biologic activity and therapeutic efficacy as a result of authentic human posttranslational modification.

Mammalian cells are most preferred, when being established, adapted, and completely cultivated under serum free conditions, and optionally in media, which are free of any protein/peptide of animal origin. Commercially available media such as Ham's F12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif.), CHO—S—Invitrogen), serum-free CHO Medium (Sigma), and protein-free CHO Medium (Sigma) are exemplary appropriate nutrient solutions. Any of the media may be supplemented as necessary with a variety of compounds, non-limiting examples of which are recombinant hormones and/or other recombinant growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics and trace elements. Any other necessary supplements may also be included at appropriate concentrations that would be known to those skilled in the art. For the growth and selection of genetically modified cells expressing a selectable gene a suitable selection agent is added to the culture medium.

Serum-Free Perfusion Medium

In another aspect a serum-free perfusion medium is provided comprising potassium ions at a concentration of 30 mM to 250 mM and a molar ratio of sodium to potassium ions of less than 1.

In some embodiments the potassium ion concentration is about 40 mM to about 200 mM, preferably about 60 mM to about 150 mM and more preferably about 80 mM to about 100 mM. In some embodiments the molar ratio of sodium to potassium is between about 0.9 and 0.1, between about 0.8 and 0.2, between about 0.7 and 0.2, preferably between about 0.6 and 0.3 and more preferably between about 0.5 and 0.4.

A preferred potassium ion concentration in the serum-free perfusion medium of the invention is about 40 mM to about 200 mM, preferably about 60 mM to about 150 mM and more preferably about 80 mM to about 100 mM. In some embodiments the molar ratio of sodium to potassium is between about 0.9 and 0.1, between about 0.8 and 0.2, between about 0.7 and 0.2, preferably between about 0.6 and 0.3 and more preferably between about 0.5 and 0.4. Examples of suitable potassium concentrations and Na:K ratios are about 40 mM to about 200 mM and a molar Na:K ratio of about 0.1 to 0.9, about 40 mM to about 200 mM and a molar Na:K ratio of about 0.2 to 0.8; about 40 mM to about 200 mM and a molar Na:K ratio of about 0.2 to 0.7; 40 mM to about 200 mM and a molar Na:K ratio of about 0.3 to 0.6; 40 mM to about 200 mM and a molar Na:K ratio of about 0.4 to 0.5; about 60 mM to about 150 mM and a molar Na:K ratio of about 0.1 to 0.9; about 60 mM to about 150 mM and a molar Na:K ratio of about 0.2 to 0.8; about 60 mM to about 150 mM and a molar Na:K ratio of about 0.2 to 0.7; about 60 mM to about 150 mM and a molar Na:K ratio of about 0.3 to 0.6; about 60 mM to about 150 mM and a molar Na:K ratio of about 0.4 to 0.5; about 80 mM to about 100 mM and a molar Na:K ratio of about 0.1 to 0.9, about 80 mM to about 100 mM and a molar Na:K ratio of about 0.2 to 0.8; about 80 mM to about 100 mM and a molar Na:K ratio of about 0.2 to 0.7; about 80 mM to about 100 mM and a molar Na:K ratio of about 0.3 to 0.6; about 80 mM to about 100 mM and a molar Na:K ratio of about 0.4 to 0.5. Particularly preferred is a potassium concentration of about 60 mM to about 150 mM and a molar Na:K ratio of about 0.6 to 0.3, even more preferred is a potassium concentration of about 60 mM to about 150 mM and a molar Na:K ratio of about 0.5 and 0.4 and even more preferred is a potassium concentration of about 80 mM to about 100 mM and a molar Na:K ratio of about 0.5 and 0.4. The potassium concentrations according to the invention together with the molar Na:K ratio according to the invention lead to a $G_0/G_1$ cell cycle arrest. Additionally the potassium concentrations according to the invention together with the molar Na:K ratio according to the invention lead to an increased cell specific productivity (qp). Thus the high potassium concentration according to the invention and the resulting low sodium concentration of the invention seem to act synergistically. Without being bound by theory it seems that the potassium concentrations according to the invention are required for the $G_0/G_1$ cell cycle arrest and the simultaneous reduction in sodium ions and hence a reduced molar Na:K ratio promotes the increased cell specific productivity.

The potassium ion may be provided as one or more potassium salt. In a preferred embodiment the one or more potassium salt is selected from the group consisting of potassium bicarbonate, potassium chloride, potassium hydroxide, L-tyrosine dipotassium salt, potassium phosphate dibasic, potassium phosphate monobasic, potassium selenite, potassium pyruvic acid, potassium glutathione, potassium D-gluconate, potassium succinate and potassium ascorbate. More preferably the potassium salt is potassium bicarbonate, potassium chloride, potassium hydroxide, L-tyrosine dipotassium salt, potassium phosphate dibasic, potassium phosphate monobasic. Preferably the osmolarity of a medium is not changed by the addition of the potassium salt. This may be achieved by replacing a sodium salt with the corresponding potassium salt. The skilled person would therefore understand that any sodium salt typically used in a cell culture medium is a preferred salt to be used as the corresponding potassium salt.

A preferred sodium ion concentration in the serum-free perfusion medium of the invention is less than 100 mM, more preferably less than 60, even more preferably 10-50 mM. The sodium ion may be provided as one or more sodium salt. In a preferred embodiment the one or more sodium salt is selected from the group consisting of sodium bicarbonate, sodium chloride, sodium hydroxide, L-tyrosine di sodium salt, sodium phosphate dibasic, sodium phosphate monobasic, sodium selenite, sodium pyruvic acid, sodium glutathione, sodium D-gluconate, sodium succinate and sodium ascorbate. More preferably the sodium salt is sodium bicarbonate, sodium chloride, sodium hydroxide, L-tyrosine disodium salt, sodium phosphate dibasic, sodium phosphate monobasic.

The osmolarity of the serum-free perfusion medium of the invention should be in the range of between 300 and 1400 mOsmol/kg, preferably between 300 and 500 mOsmol/kg, more preferably between 330 and 450 mOsmol/kg and even more preferably between 360 and 390 mOsmol/kg. Wherein the osmolarity is provided as mOsmol/kg water.

The serum-free perfusion medium of the invention may be chemically defined and/or hydrolysate-free. Hydrolysate-free means that the medium does not contain protein hydrolysates from animal, plant (soybean, potato, rice), yeast or other sources. Typically a chemically defined medium is hydrolysate-free. In any case the serum-free perfusion medium should be free of compounds derived from animal sources, particularly proteins or peptides derived and isolated from an animal (this does not include recombinant proteins produced cell culture). Preferably the serum-free perfusion medium is protein-free or protein-free except for recombinant insulin and/or insulin-like growth factor. More preferably the serum-free perfusion medium is chemically defined and protein-free or protein-free except for recombinant insulin and/or insulin-like growth factor.

In yet another aspect a use of the serum-free perfusion medium of the invention for culturing mammalian cells in a perfusion culture during production phase or for reducing the total cell bleed volume in a perfusion culture is provided. Alternatively a use of the serum-free perfusion medium of the invention for increasing protein production in a perfusion cell culture is provided. The use of the medium is as disclosed for the serum-free perfusion medium (of step (c)) used in the methods of the inventions.

EXAMPLES

Example 1: Effect of Cell Bleed on Total Productivity

A CHO cell line producing a monoclonal antibody was cultured in 3 L glass perfusion bioreactors at a 2 L working volume utilizing two different recirculation devices as indicated: ATF #1 and ATF #2 were replicates using an ATF 2 device (Repligen, Waltham, Mass.) and the TFF bioreactor used a centrifugal pump (Levitronix, Zurich, Switzerland). The hollow fiber used was a polyethersulfone (PES) with a 0.2 μm pore size and 1 mm lumen ID. A perfusion media with the concentration ratio Na:K 9 was used for the entire duration of cell culture. Recirculation and perfusion rates were kept constant across all three reactors. Titer was measured for the harvest (permeate) stream (recovered product) and bioreactor contents (reactor titer) daily to account for any product sieving across the hollow fiber with titer of the cell bleed assumed to be identical to bioreactor titer. The total grams produced at the end of cell culture (day 29) were estimated according to the following calculations:

$$\text{Recovered product} = \sum_{day_0}^{day_{29}} \left[ \text{permeate volume}_{day_n-day_{n-1}} \times \frac{\text{permeate titer}_{day_n} + \text{permeate titer}_{day_{n-1}}}{2} \right]$$

$$\text{Product lost: bleed} = \sum_{day_0}^{day_{29}} \left[ \text{bleed volume}_{day_n-day_{n-1}} \times \frac{\text{reactor titer}_{day_n} + \text{reactor titer}_{day_{n-1}}}{2} \right]$$

Product lost:reactor=Working volume$_{reactor}$×reactor titer$_{day29}$

Total produced=Recovered product+product lost: bleed+product lost:reactor

As may be taken from FIG. 1, the cell bleed can account for about 30% total product loss in a steady state perfusion process.

Example 2: Cell Growth and Productivity Response to Change in Na+/K+ Concentrations in a Deep Well Model of Perfusion A serum-free chemically defined media for perfusion was used as the background for all media experiments. The levels of $Na^+$ and $K^+$ were altered where indicated to reach $Na^+/K^+$ ratios between 0.3 to infinity (no $K^+$). This was achieved by interchanging media components sodium chloride (NaCl), sodium hydroxide (NaOH), and sodium bicarbonate ($NaHCO_3$) with the respective potassium forms to obtain the final Na and K concentration as shown in Table 2 for all tested media below without changing osmolarity. Final medium osmolarity was between 360-390 mosmol/kg water for all conditions. A recombinant Chinese Hamster Ovary (CHO) cell line (CHO-DG44) producing monoclonal antibody mAb 1 (IgG1) was used. Thawed inoculum cultures were grown in serum-free chemically defined inoculation medium and maintained in shake flasks until the target cell density were reached. Cells for deep well plate work were inoculated directly into AXYGEN 24 well pre-sterilized deep well plates (Neta Scientific Inc, Hainesport, N.J.). A starting cell density of 20e6 cells/mL was used for deep well plate model work to simulate the high cell density phase of perfusion and to test media depth. To achieve such high cell densities from shake flask culture, the necessary volume was centrifuged at 1000 rpm for 5 minutes and the cell pellet resuspended in perfusion media to the desired density before distribution into deep well plates. The working volume per well was 3 mL. Cells were grown at 33° C. with 5% $CO_2$, 80% humidity, and 200 rpm in an incubator with a 5.0 cm orbit diameter. Medium exchanges were performed daily by centrifuging the plate at 1200 rpm for 5 minutes, removing supernatant, and resuspending cells in fresh media at an exchange rate of ⅔ vessel volumes per day (VVD).

Cell cycle analysis was performed on day 5 of deep well culture. Cells were grown in medium containing either Na:K 2 (K=37 mM) or Na:K 0.5 (K=76 mM) and fixed on day 5 by a 2× wash in cold PBS before suspension in 70% ethanol. Cells were subsequently stained with propidium iodide with RNase (BD Biosciences) for DNA content and analyzed by flow cytometry on a GUAVA EASYCYTE flow cytometry (EMD Millipore).

TABLE 2

| mM | Na:K 9 | Na:K 2 | Na:K 1 | Na:K 0.5 | Na:K 0.4 |
|---|---|---|---|---|---|
| NaCl (mM) | 16 | 16 | 0 | 0 | 0 |
| NaHCO₃ (mM) | 25 | 0 | 0 | 0 | 0 |
| NaOH | 28 | 28 | 16 | 0 | 0 |
| Na+ (mM) from other | 34 | 34 | 34 | 34 | 34 |
| KCl (mM) | 12 | 12 | 12 | 39 | 39 |
| KHCO₃ (mM) | 0 | 25 | 25 | 25 | 25 |
| KOH | 0 | 0 | 12 | 12 | 30 |
| Total Na+ (mM) | 103 | 78 | 50 | 34 | 34 |
| K+ (mM) | 12 | 37 | 49 | 76 | 94 |
| Total Na+ and K+ (mM) | 115 | 115 | 99 | 110 | 128 |
| Molar Na:K | 8.6 | 2.1 | 1 | 0.45 | 0.36 |

Figure 2:
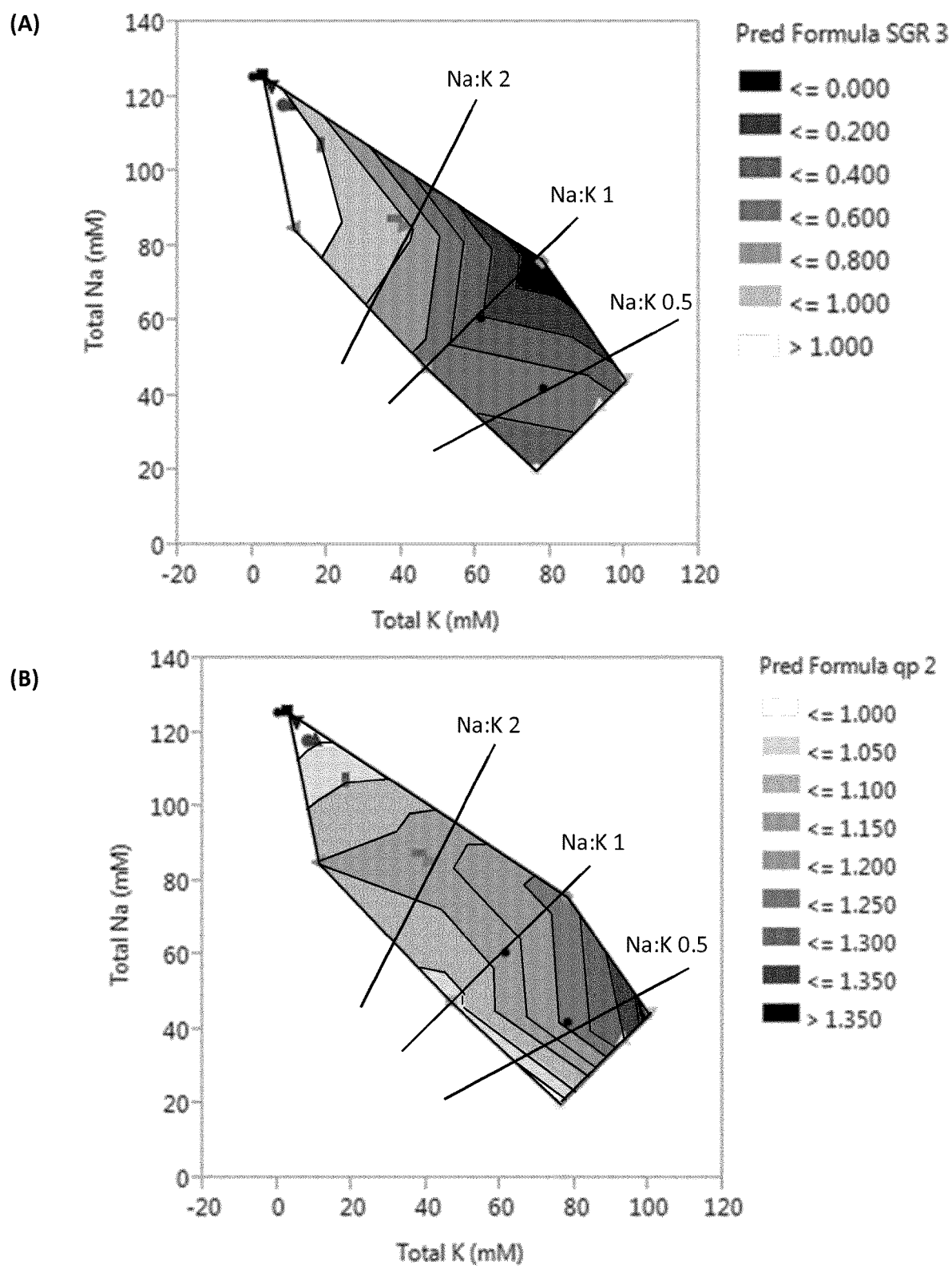
FIG. 2: Cell growth and productivity response to change in Na+/K+ concentrations in a deep-well model of perfusion. Degree of response is expressed as proportion of difference from the control condition Na=78 mM, K=37 mM (Na:K 2) where a score of 0.4 corresponds to an area where anticipated response at the indicated Na+ and K+ levels is 40% of the control (Na:K 2) condition. Contour plots of cumulative specific growth rate (SGR) (A) and cumulative cell specific productivity (qp) (B) are shown for the range of concentrations tested in a CHO cell line producing monoclonal antibody mAb1. Actual data points for conditions tested are shown as markers in both contour plots. Representative viable cell density (VCD) and viability plots are shown in panels (C) and (D) respectively for the entire time course of cell culture. The viable cell density (VCD) is given in e5 cells/mL, which is the technical spelling for "$10^5$ cells/mL". Differences between different conditions were observed in viable cell density over time while viability remained consistently high (>85%) throughout the entire 7 days of culture.
Figure 2:
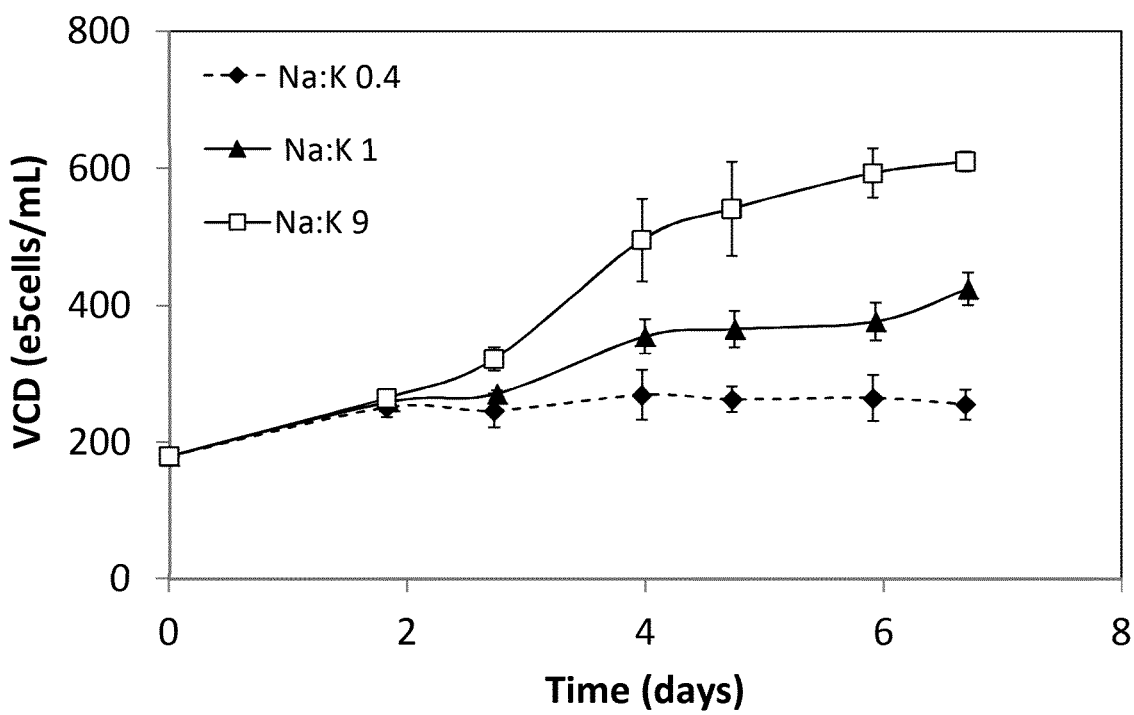
Figure 2:
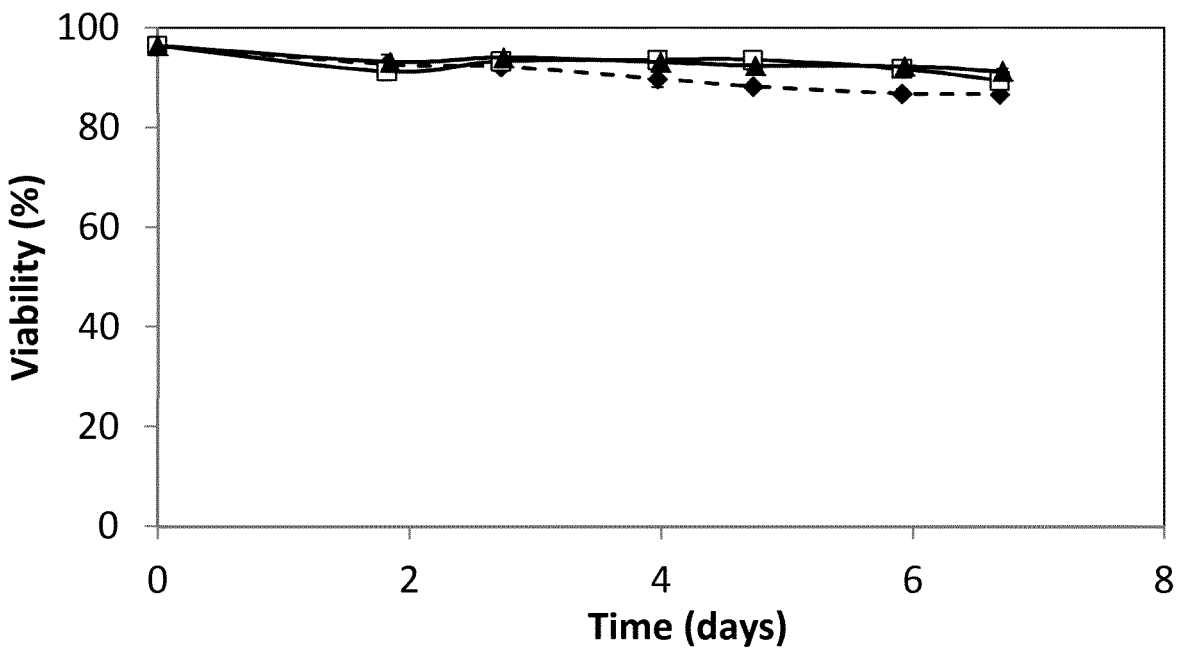

Contour plots of cumulative specific growth rate (SGR) and cumulative cell specific productivity (qp) are shown in FIGS. 2A and B for the range of concentrations tested. Degree of response is expressed as proportion of difference from the control condition Na=78 mM, K=37 mM (Na:K 2) where darker areas represent conditions of lower cell growth or higher specific productivity. Dotted lines represent the Na:K ratios as marked. Both cell growth and cell specific productivity are dependent on Na and K concentrations where higher productivity and slower cell growth occur at higher K levels. Higher Na:K ratios (Na:K>2) encompass regions of less productivity and higher cell growth compared to a Na:K ratio of less than 1.

Representative viable cell density (VCD) and viability plots are shown for the entire time course of the cell culture in FIGS. 2C and D. Reducing the Na:K ration resulted in a reduced viable cell density over time, indicating a lower specific growth rate (FIG. 2C) while the viability remained consistently high (>85%) throughout the entire 7 days of culture (FIG. 2D).

Figure 3:
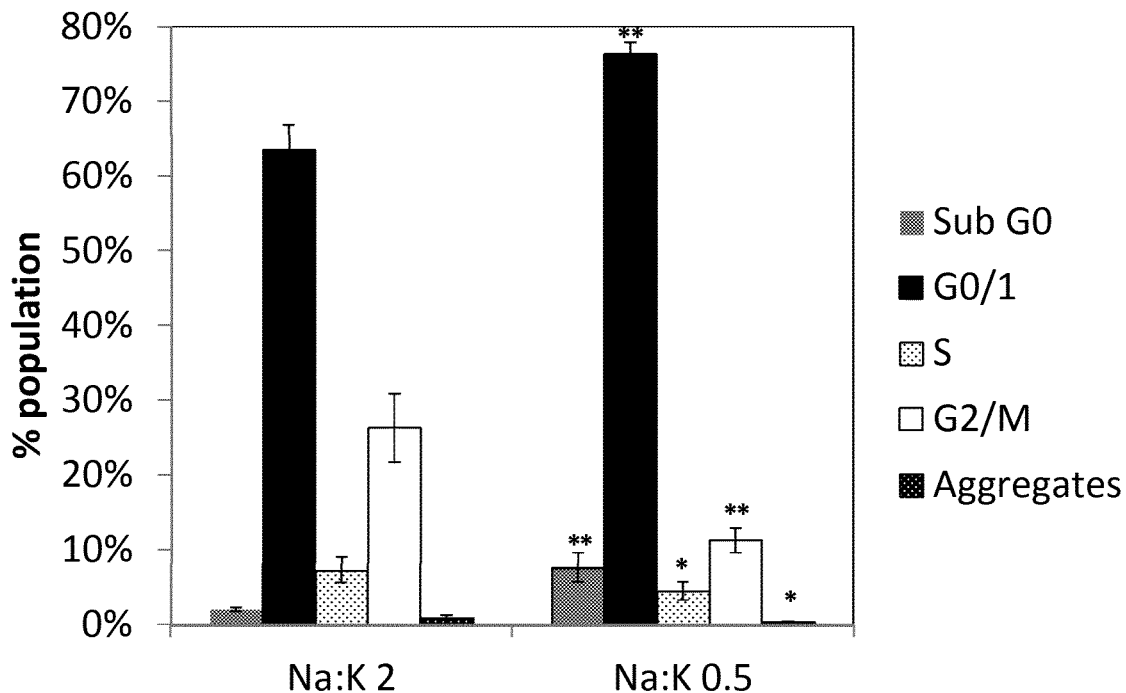
FIG. 3: Cell cycle analysis of a CHO cell line producing monoclonal antibody mAb1 treated with different Na+/K+ concentrations in a deep-well model of perfusion. Cell cycle analysis was performed using propidium iodide staining and FACS analysis. Bar plots of cells in sub G0, G0/1, S and G2/M phase and cell aggregates are shown in panel (A) and G0/1:G2M ratios are shown in panel (B) for the tested concentration ratios Na:K 2 (37 mM potassium) and Na:K 0.5 (76 mM potassium) Two tailed student's t-test was performed to determine statistical significance vs. Na:K 2 (* $p<0.05$; ** $p<0.001$).
Figure 3:
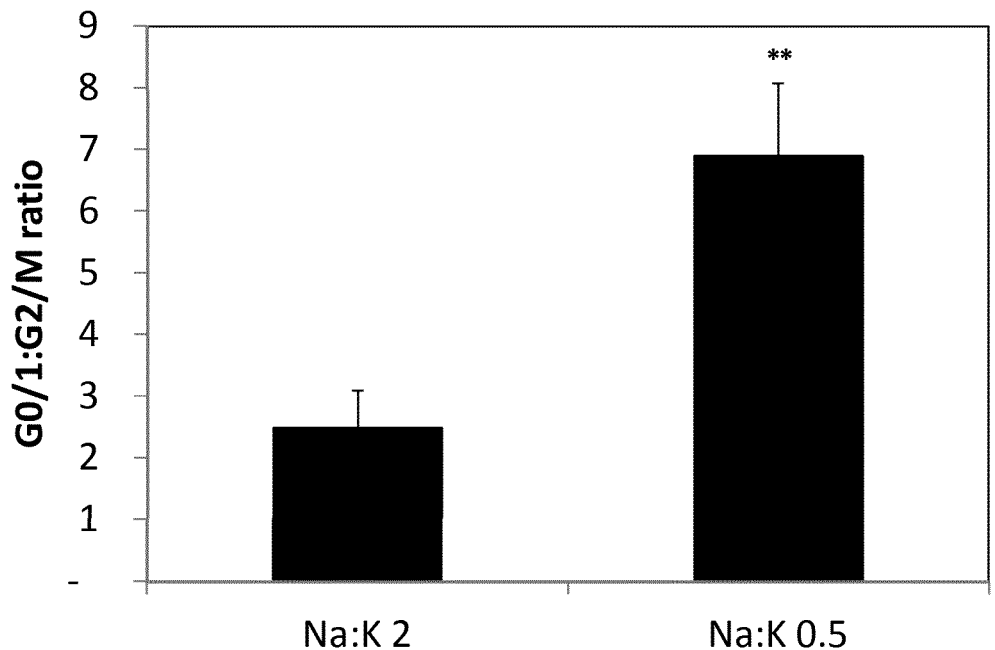

Results of the cell cycle analysis of CHO cells treated with different Na+/K+ concentrations is shown in FIG. 3. The proportion of cells in the sub G0 and G0/1 phase increased, while the portion of cells in S and G2/M phase decreased in CHO cells cultured in the Na:K 0.5 medium compared to the Na:K 2 medium (FIG. 3A). This is even more apparent from FIG. 3B, showing the G0/1:G2/M ratio for CHO cells cultured in the Na:K 0.5 medium compared to the Na:K 2 medium. This confirms that lowering the sodium to potassium ratio arrests cells in the G0/1 phase.

Example 3: Cell Performance in 2 L Perfusion Reactors

Three CHO cell lines expressing different monoclonal antibodies were assessed. Cells for bioreactor cultures were grown in the same perfusion medium (9 $Na^+/K^+$) until a target cell density was reached before either switching to a Na:K 0.5 medium (~76 mM K) or remaining in the Na:K 9 medium (12 mM $K^+$). The hollow fiber used in all perfusion bioreactors was made of polyethersulfone (PES) with a 0.2 µm pore size and 1 mm lumen ID. The recirculation device used in all examples was an ATF 2 system (Repligen, Waltham, Mass.) or a TFF system using a centrifugal pump (Levitronix, Zurich, Switzerland). The two systems had been previously demonstrated to be interchangeable at the 2 L scale. All studies were conducted in 3 L glass stirred tank bioreactors at a 2 L working volume (Applikon Biotechnology, Delft, Netherlands). A minimum cell specific perfusion rate was established for each cell line and ranged between 0.03 to 0.08 nL/cell/day at steady state. This perfusion rate was kept the same between different media conditions for the same cell line. Viable cell density was kept constant over time by a cell bleed that was controlled by online feedback using an INCYTE probe (Hamilton, Reno, Nev.). The cell lines used in this experiments were CHO-DG44 cells expressing mAb1 (exemplifying a low producing cell line; qp<20 pg/cell/day), CHO-K1 cells expressing mAb2 (exemplifying a moderate producing cell line; 20 pg/cell/day<qp<40 pg/cell/day), and CHO-K1 cells expressing mAb3 (exemplifying a high producing cell line; qp>50 pg/cell/day).

Further, the specific effect on glycosylation patterns, acidic and basic species or high and low molecular species were analyzed in the three cell lines. Permeate was collected daily over the duration of cell culture for reactors on the reduced Na:K ratio as well as the reactors on the control media (Na:K 9) for all three cell lines. Acidic and basic species was measured by cation exchange chromatography (CEX), high and low molecular weight species by size exclusion chromatography (SEC), and N-glycans by 2-AA hydrophilic interaction liquid chromatography (HILIC). Chromatograms were analyzed for species percentages.

Figure 4:
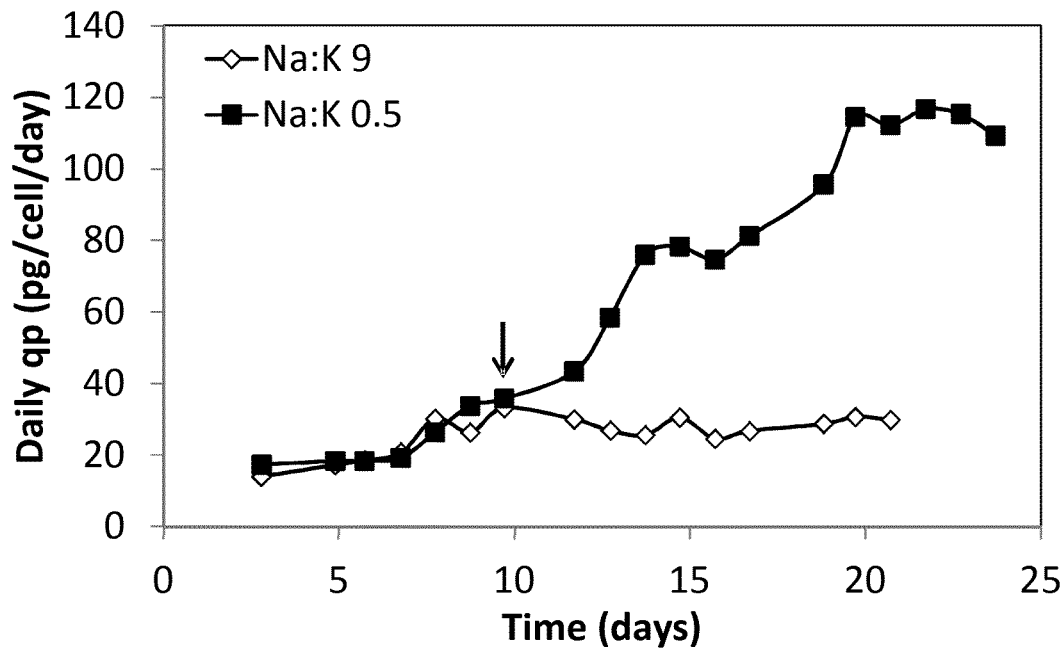
FIG. 4: Cell growth and productivity response to change in Na+/K+ concentrations in 2 L perfusion reactors. Representative diagrams are shown for daily qp in panel (A), for daily specific growth rate (SGR) in panel (B), for viability in panel (C) and for cell bleed flow rate in panel (D) for a CHO-K1 cell line producing monoclonal antibody mAb2. Cells for bioreactor cultures were grown in the same perfusion medium (9 Na+/K+) until a target cell density was reached before either switching to a Na:K 0.5 medium (~76 mM K) (filled squares) or remaining on the Na:K 9 medium (12 mM K) (empty diamonds). The arrow indicates the time point (day 10) when media was switched from the Na:K 9 ratio medium to the lowered Na:K 0.5 ratio medium.
Figure 4:
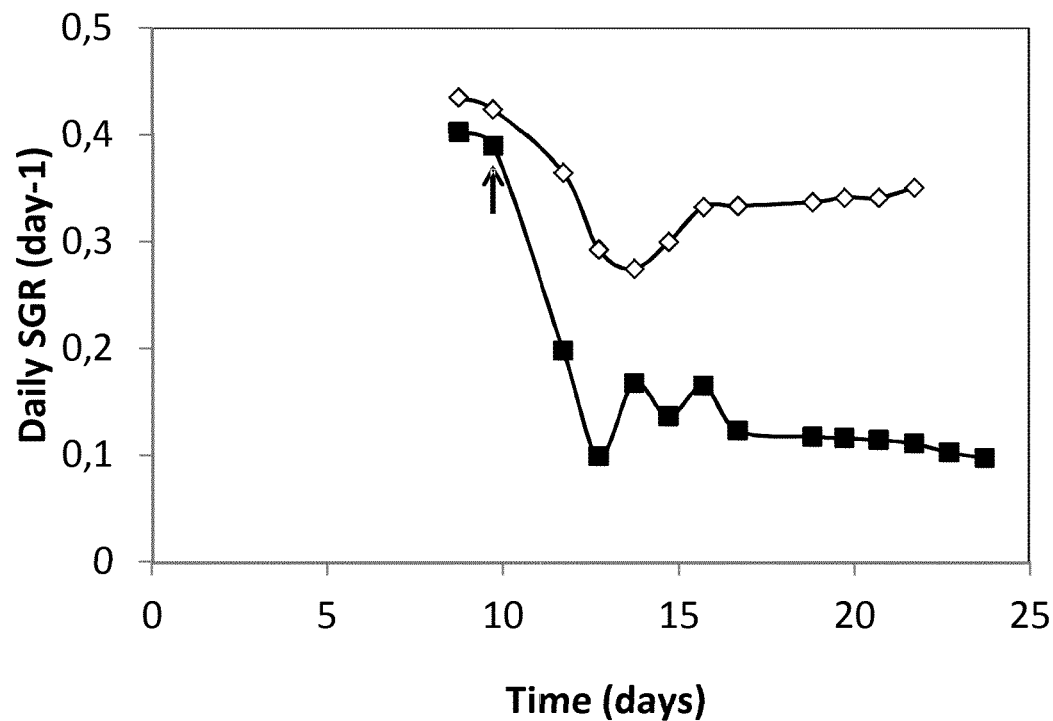
Figure 4:
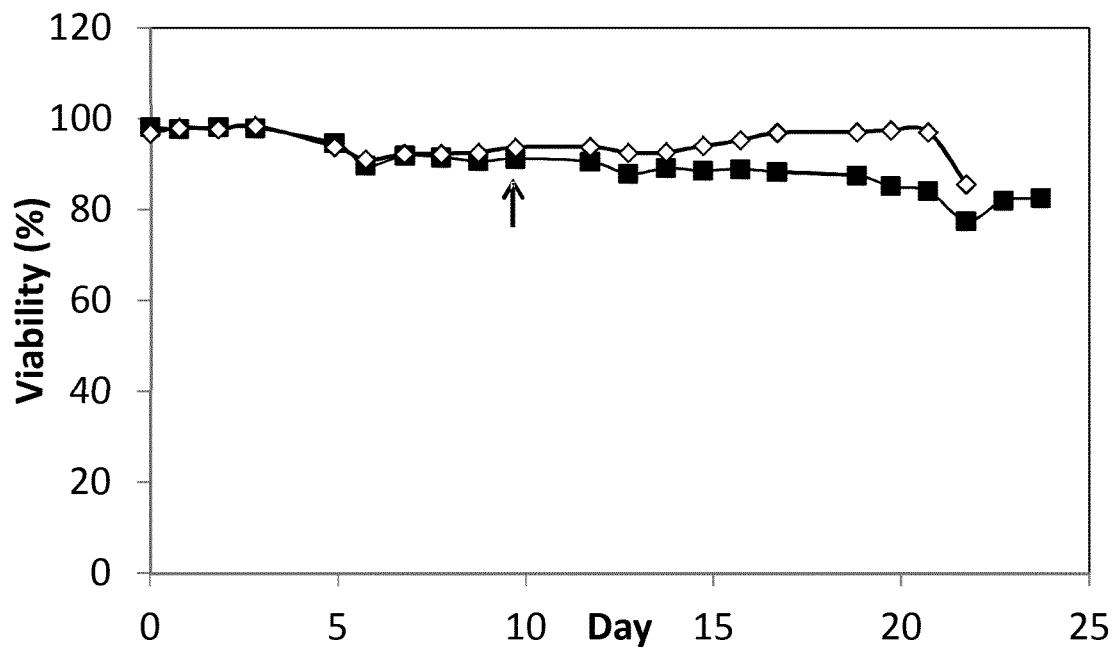
Figure 4:
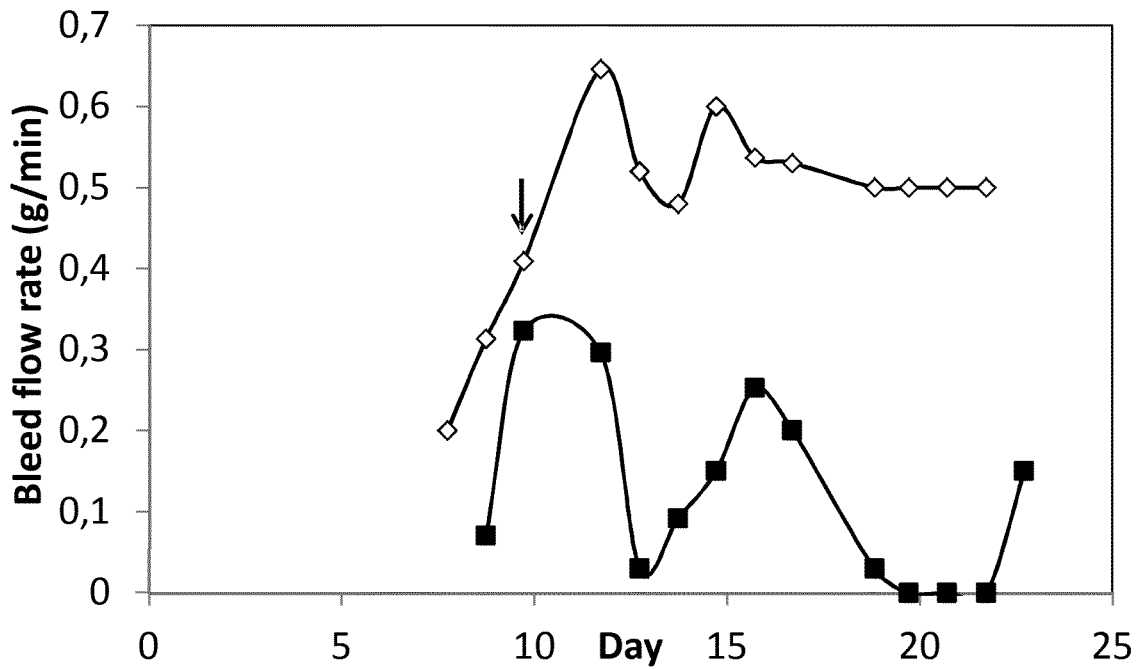

Representative daily qp, SGR, viability and cell bleed plots are shown for the moderate producer (mAb2) in FIGS. 4A to D. As may be taken from FIG. 4A, cell specific productivity increased right after the culture medium has been switched to Na:K 0.5 medium on day 10 compared to control cells that were maintained in Na:K 9 medium. At the same time the specific growth rate declined faster and to a lower overall level compared to control cells (FIG. 4B). This is also reflected by the much lower bleed flow rate (FIG. 4D) required to maintain a constant viable cell density (data not shown). Reducing the Na:K ratio to 0.5 did not affect cell viability (FIG. 4C).

TABLE 3

| Cell line | Na:K 0.5/Na:K 9 (% difference) Total bleed volume |
|---|---|
| CHO-DG44 mAb1 | 48% |
| CHO-K1 mAb2 | 32% |
| CHO-K1 mAb3 | 51% |

The final total bleed volume for all three cell lines are shown in Table 3. The bleed volume is normalized to the control (Na/K 9 condition) and expressed as percent of Na/K 0.5 condition versus the Na/K 9 condition.

Figure 5:
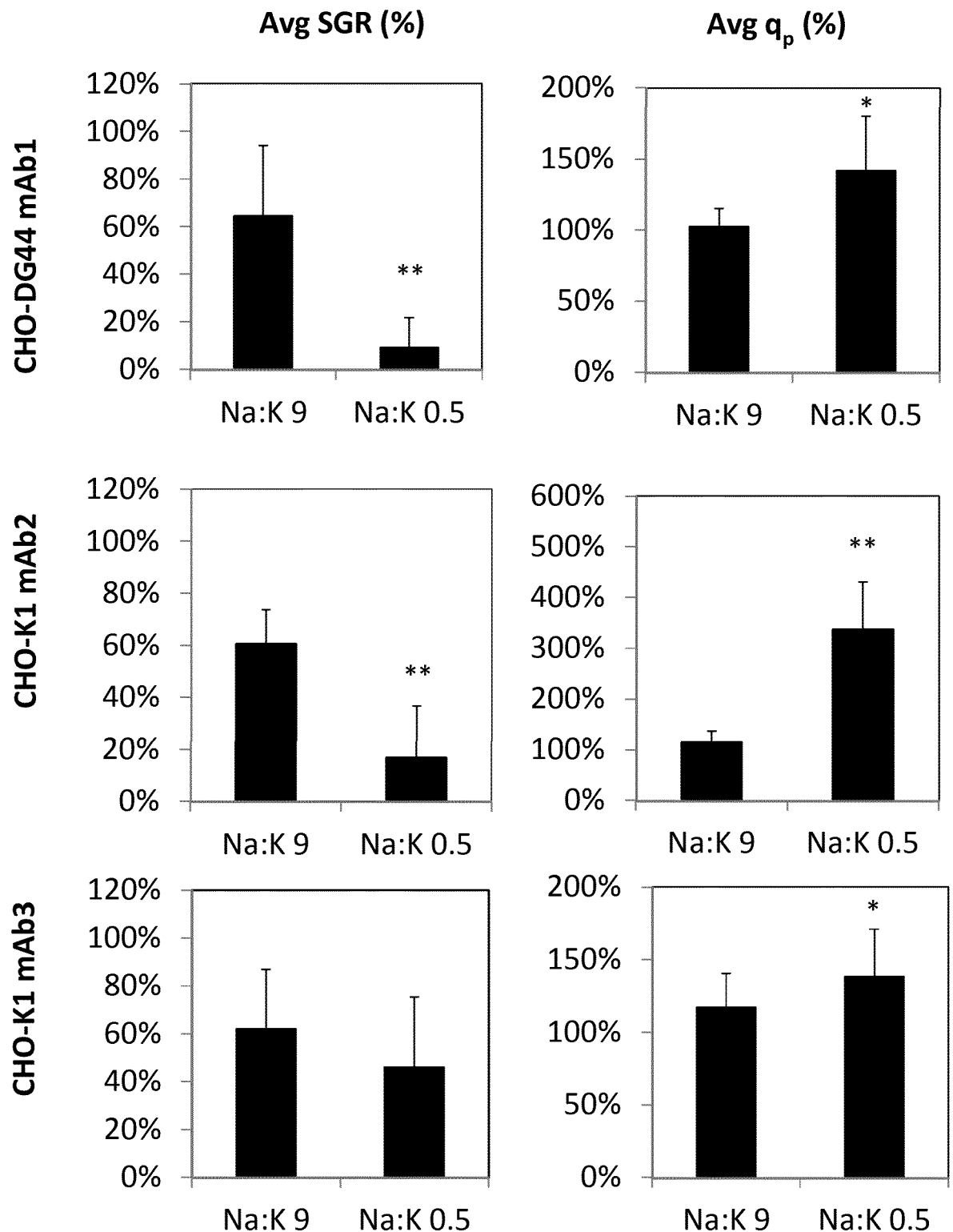
FIG. 5: Cell growth and productivity response to change in Na+/K+ concentrations in 2 L perfusion reactors on day 22 of perfusion culture. Cells for bioreactor cultures were grown in the same perfusion medium (9 Na+/K+) until a target cell density was reached before either switching to a 0.5 Na/K medium (76 mM K) or remaining on the 9 Na/K medium (12 mM K). Differences in cumulative average qp and average specific growth rate (SGR) between the two different media are shown in representative plots for three CHO cell lines expressing monoclonal antibodies mAb1 (CHO-DG44 mAb1), mAb2 (CHO-K1 mAb2) or mAb3 (CHO-K1 mAb3). Average qp and average SGR is expressed as average qp and SGR after the media switch normalized to their respective values prior to the media switch (ie day 10-22/days 0-10 for mAb1 and 3 and day 12-22/day 0-12 for mAb2). Two tailed student's t-test was performed to determine statistical significance (*$p<0.05$, **$p<0.001$).

Differences in average qp and SGR between the two different media on day 22 of perfusion culture are shown in FIG. 5 for the tree different CHO cells lines expressing different monoclonal antibodies and differing in their productivity. Average qp and average SGR are expressed as average qp and SGR after the media switch normalized to their respective values prior to the media switch (ie day 10-22/days 0-10 for mAb1 and 3 and day 12-22/day 0-12 for mAb2). All three CHO cell lines show a reduction in specific growth rate following the switch to Na:K 0.5 medium. This effect is most pronounced in CHO-DG44 mAb1 and in CHO-K1 mAb2, with an even stronger effect in CHO-DG44 mAb1. Although there is also a trend toward a reduced specific growth rate in CHO-K1 mAb3 (IgG4) with a medium having a reduced Na:K ratio, this difference is not statistically significant. Assessment of the daily growth rate for CHO-K1 mAb3 cells revealed that growth rate after switching the medium to lower Na;K ratio decreased over time to about 0.2 relative to the SGR on the day before medium switch, while the growth rate in control cultures remained stable until day 22 at about 0.6 relative to the SGR on the day before medium switch. Compared to the other two cell lines tested, CHO-DG44 mAb3 seemed to have a slower response time to the medium switch. It is therefore conceivable that the average growth rate would show a significant difference had the culture duration been extended. At the same time the cell specific productivity is statistically significantly increased in all three cell lines when cultured in a medium with a reduced Na:K ratio. The effect was most pronounced for CHO-K1 mAb2. The increase for CHO-DG44 mAb1 and CHO-K1 mAb3 was at a similar slightly less pronounced level, but still statistically significant.

No specific effect on glycosylation patterns, acidic and basic species or high and low molecular species was observed over the three cell lines tested.

In view of the above it will be appreciated that the present invention also relates to the following items:

Items

1. A method of culturing mammalian cells expressing a heterologous protein in a perfusion cell culture comprising:
   (a) inoculating mammalian cells expressing a heterologous protein in a serum-free culture medium;
   (b) culturing the mammalian cells during growth phase by perfusion with a serum-free perfusion medium; and
   (c) culturing the mammalian cells during production phase by perfusion with a serum-free perfusion medium comprising potassium ions at a concentration of 30 mM to 250 mM and a molar ratio of sodium to potassium ions of less than 1, wherein step (b) is optional.
2. A method of reducing cell bleeding in a perfusion cell culture expressing a heterologous protein comprising:
   (a) inoculating mammalian cells expressing a heterologous protein in a serum-free culture medium;
   (b) culturing the mammalian cells during growth phase by perfusion with a serum-free perfusion medium; and
   (c) culturing the mammalian cells during production phase by perfusion with a serum-free perfusion medium comprising potassium ions at a concentration of 30 mM to 250 mM and a molar ratio of sodium to potassium ions of less than 1, wherein step (b) is optional.
3. A method of increasing protein production in a perfusion cell culture expressing a heterologous protein comprising:
   (a) inoculating mammalian cells expressing a heterologous protein in a serum-free culture medium;
   (b) culturing the mammalian cells during growth phase by perfusion with a serum-free perfusion medium; and
   (c) culturing the mammalian cells during production phase by perfusion with a serum-free perfusion medium comprising potassium ions at a concentration of 30 mM to 250 mM and a molar ratio of sodium to potassium ions of less than 1, wherein step (b) is optional.
4. The method of any one of items 1 to 3, wherein step (c) further comprises maintaining a cell density by cell bleeding.
5. The method of item 4, wherein cell bleeding is reduced compared to a perfusion cell culture using the same serum-free perfusion medium comprising potassium ions at a concentration of less than 30 mM and a molar ratio of sodium to potassium of more than 2 and cultured under the same conditions.
6. The method of any one of the preceding items, wherein the potassium ion concentration is about 40 mM to about 200 mM, preferably about 60 mM to about 150 mM and more preferably about 80 mM to about 100 mM.
7. The method of any one of the preceding items, wherein the molar ratio of sodium to potassium is between about 0.9 and 0.1, between about 0.8 and 0.2, between about 0.7 and 0.2, preferably between about 0.6 and 0.3 and more preferably between about 0.5 and 0.4.
8. The method of any one of the preceding items, wherein the potassium ion is provided as one or more potassium salt.
9. The method of item 8, wherein the one or more potassium salt is selected from the group consisting of potassium bicarbonate, potassium chloride, potassium hydroxide, L-tyrosine dipotassium salt, potassium phosphate dibasic, potassium phosphate monobasic, potassium selenite, potassium pyruvic acid, potassium glutathione, potassium D-gluconate, potassium succinate and potassium ascorbate.
10. The method of item 9, wherein the one or more potassium salt substitutes the corresponding sodium salt in the serum-free perfusion culture medium.
11. The method of item 10, wherein the potassium ion is provided as one or more potassium salt and the one or more potassium salt substitutes the corresponding sodium salt in the serum-free perfusion medium of step b).
12. The method of any one of the preceding items, wherein the mammalian cell is a Chinese hamster ovary (CHO) cell.
13. The method of item 12, wherein the CHO cell is a CHO-DG44 cell, a CHO-K1 cell, a CHO DXB11 cell, a CHO-S cell, a CHO GS deficient cell or a derivative of any of these cells.
14. The method of any one of the preceding items, wherein the serum-free culture medium of step (a) and the serum-free perfusion medium of step (b) comprise potassium ions at less than 30 mM.
15. The method of any one of the preceding items, wherein perfusion in step (b) begins on or after day 2 of the cell culture.
16. The method of any one of the preceding items wherein the perfusion comprises continuous perfusion.
17. The method of any one of the preceding items, wherein the perfusion rate increases after perfusion has started.
18. The method of item 17, wherein the perfusion rate increases from less or equal to 0.5 vessel volumes per day to 5 vessel volumes per day.
19. The method of item 18, wherein the perfusion rate increases from less or equal to 0.5 vessel volumes per day to 2 vessel volumes per day.
20. The method of any one of the preceding items, further comprising harvesting the heterologous protein from the perfusion cell culture.
21. The method of any one of the preceding items, wherein the heterologous protein is a therapeutic protein.
22. The method of item 21, wherein the therapeutic protein is selected from the group consisting of an antibody, a fusion protein, a cytokine and a growth factor.
23. The method of any one of the preceding items, wherein the serum-free perfusion medium is chemically defined.
24. The method of any one of the preceding items, wherein the serum-free perfusion medium is hydrolysate-free.
25. The method of any one of the preceding items, wherein the serum-free perfusion medium is protein-free except for recombinant insulin and/or insulin-like growth factor.
26. The method of any one of items 1 to 24, wherein the serum-free perfusion medium is protein-free.
27. The method of any one of items 1 to 26, wherein step (c) is started once a cell density of $10 \times 10^6$ cells/ml to about $120 \times 10^6$ cells/ml is reached.
28. The method of any one of items 1 to 27, wherein the osmolarity of the medium is between 300 and 1400 mOsmol/kg, preferably between 300 and 500 mOsmol/kg.
29. A method of producing a therapeutic protein using the method of any one of items 1 to 28.
30. The method of item 29, wherein the heterologous protein expressed by the mammalian cell is a therapeutic protein and wherein the therapeutic protein is purified and formulated into a pharmaceutically acceptable formulation.
31. A serum-free perfusion medium comprising potassium ions at a concentration of 30 mM to 250 mM and a molar ratio of sodium to potassium ions of less than 1.

32. The serum-free perfusion medium of item 31, wherein the potassium ion concentration is about 40 mM to about 200 mM, preferably about 60 mM to about 150 mM and more preferably about 80 mM to about 100 mM.

33. The serum-free perfusion medium of item 31 or 32, wherein the molar ratio of sodium to potassium is between about 0.9 and 0.1, between about 0.8 and 0.2, between about 0.7 and 0.2, preferably between about 0.6 and 0.3 and more preferably between about 0.5 and 0.4.

34. The serum-free perfusion medium of any one of items 31 to 33, wherein the potassium ion is provided as one or more potassium salt.

35. The serum-free perfusion medium of item 34, wherein the one or more potassium salt is selected from the group consisting potassium bicarbonate, potassium chloride, potassium hydroxide, L-tyrosine dipotassium salt, potassium phosphate dibasic, potassium phosphate monobasic, potassium selenite, potassium pyruvic acid, potassium glutathione, potassium D-gluconate, potassium succinate and potassium ascorbate.

36. The serum-free perfusion medium of item 35, wherein the one or more potassium salt and/or potassium hydroxide substitutes the corresponding sodium salt in the serum-free perfusion culture medium.

37. The serum-free perfusion medium of any one of items 31 to 36, wherein the serum-free perfusion medium is chemically defined.

38. The serum-free perfusion medium of any one of items 31 to 37, wherein the serum-free perfusion medium is hydrolysate-free.

39. The serum-free perfusion medium of any one of items 31 to 38, wherein the serum-free perfusion medium is protein-free except for recombinant insulin and/or insulin-like growth factor.

40. The serum-free perfusion medium of any one of items 31 to 38, wherein the serum-free perfusion medium is protein-free.

41. The serum-free perfusion medium of any one of items 31 to 40, wherein the osmolarity of the medium is between 300 and 1400 mOsmol/kg, preferably between 300 and 500 mOsmol/kg.

42. Use of the serum-free perfusion medium of any one of items 31 to 41 for culturing mammalian cells in a perfusion culture during production phase.

43. Use of the serum-free perfusion medium of any one of items 31 to 41 for reducing the total cell bleed volume in a perfusion culture.

44. Use of the serum-free perfusion medium of any one of items 31 to 41 for increasing protein production in a perfusion cell culture.

45. Use of the serum-free perfusion medium of any one of items 31 to 41 for increasing cell specific protein production in a perfusion cell culture.

The invention claimed is:

1. A method of culturing mammalian cells expressing a heterologous protein in a perfusion cell culture comprising:
   (a) inoculating mammalian cells expressing a heterologous protein in a serum-free culture medium;
   (b) culturing the mammalian cells during growth phase by perfusion with a serum-free perfusion medium; and
   (c) culturing the mammalian cells during production phase by perfusion with a serum-free perfusion medium comprising potassium ions at a concentration of 30 mM to 250 mM and a molar ratio of sodium to potassium ions of less than 1,
   wherein the osmolarity of the serum-free perfusion media is between 300 and 500 mOsmol/kg,
   wherein step (b) is optional,
   and wherein step (c) further comprises maintaining a cell density by cell bleeding, wherein cell bleeding is reduced compared to a perfusion cell culture using the same serum-free perfusion medium comprising potassium ions at a concentration of less than 30 mM and a molar ratio of sodium to potassium of more than 2 and cultured under the same conditions.

2. The method of claim 1, wherein the potassium ion concentration is about 40 mM to about 200 mM, or about 60 mM to about 150 mM or about 80 mM to about 100 mM.

3. The method of claim 1, wherein the molar ratio of sodium to potassium is between about 0.9 and 0.1, between about 0.8 and 0.2, between about 0.7 and 0.2, between about 0.6 and 0.3 or between about 0.5 and 0.4.

4. The method of claim 1, wherein the potassium ion is provided as one or more potassium salt, wherein the one or more potassium salt is selected from the group consisting of potassium bicarbonate, potassium chloride, potassium hydroxide, L-tyrosine dipotassium salt, potassium phosphate dibasic, potassium phosphate monobasic, potassium selenite, potassium pyruvic acid, potassium glutathione, potassium D-gluconate, potassium succinate and potassium ascorbate, or wherein the one or more potassium salt substitutes the corresponding sodium salt in the serum-free perfusion culture medium, or wherein the potassium ion is provided as one or more potassium salt and the one or more potassium salt substitutes the corresponding sodium salt in the serum-free perfusion medium of step (b).

5. The method of claim 1, wherein the mammalian cell is a Chinese hamster ovary (CHO) cell, a CHO-DG44 cell, a CHO-K1 cell, a CHO DXB11 cell, a CHO-S cell, a CHO GS deficient cell or a derivative of any of these cells.

6. The method of claim 1, wherein the heterologous protein is a therapeutic protein, selected from the group consisting of an antibody, a fusion protein, a cytokine and a growth factor.

7. A serum-free perfusion medium comprising potassium ions at a concentration of 30 mM to 250 mM and a molar ratio of sodium to potassium ions of less than 1, wherein the osmolarity of the serum-free perfusion media is between 300 and 500 mOsmol/kg.

8. A method of producing a therapeutic protein using the method of claim 1.

9. A method for culturing mammalian cells in a perfusion culture during a production phase, wherein the method comprises culturing the mammalian cells in the serum-free perfusion medium of claim 7.

10. A method of reducing cell bleeding in a perfusion cell culture expressing a heterologous protein comprising:
   (a) inoculating mammalian cells expressing a heterologous protein in a serum-free culture medium;
   (b) culturing the mammalian cells during growth phase by perfusion with a serum-free perfusion medium; and
   (c) culturing the mammalian cells during production phase by perfusion with a serum-free perfusion medium comprising potassium ions at a concentration of 30 mM to 250 mM and a molar ratio of sodium to potassium ions of less than 1, wherein the osmolarity of the serum-free perfusion media is between 300 and 500 mOsmol/kg,
   wherein step (b) is optional,
   and wherein step (c) further comprises maintaining a cell density by cell bleeding, wherein cell bleeding is reduced compared to a perfusion cell culture using the same serum-free perfusion medium comprising potassium ions at a concentration of less than 30 mM and a molar ratio of sodium to potassium of more than 2 and cultured under the same conditions.

11. A method for reducing the total cell bleed volume in a mammalian cell perfusion culture, wherein the method comprises culturing the mammalian cells in the serum-free perfusion medium of claim 7.

\* \* \* \* \*